United States Patent
Hammer et al.

(10) Patent No.: US 11,819,620 B2
(45) Date of Patent: Nov. 21, 2023

(54) DIRECTIONAL LOCK FOR INTERFACE HEADGEAR ARRANGEMENT

(71) Applicant: Fisher & Paykel Healthcare Limited, Auckland (NZ)

(72) Inventors: Jeroen Hammer, Auckland (NZ); Vitaly Kapelevich, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/171,159

(22) Filed: Feb. 17, 2023

(65) Prior Publication Data
US 2023/0201510 A1    Jun. 29, 2023

Related U.S. Application Data

(63) Continuation of application No. 16/085,291, filed as application No. PCT/IB2017/051522 on Mar. 16, 2017, now Pat. No. 11,607,518.
(Continued)

(51) Int. Cl.
*A61M 16/06* (2006.01)
*F16G 11/10* (2006.01)
(Continued)

(52) U.S. Cl.
CPC ....... *A61M 16/0683* (2013.01); *A01K 1/0613* (2013.01); *A42B 1/02* (2013.01);
(Continued)

(58) Field of Classification Search
CPC .......... A61M 16/0683; A61M 16/0605; A01K 1/0613; A42B 1/02; A42B 1/04;
(Continued)

(56) References Cited

U.S. PATENT DOCUMENTS

| 301,111 A | 7/1884 | Genese |
|---|---|---|
| 472,238 A | 4/1892 | Van Orden |

(Continued)

FOREIGN PATENT DOCUMENTS

| CA | 996301 | 9/1976 |
|---|---|---|
| CA | 1311662 | 12/1992 |

(Continued)

OTHER PUBLICATIONS cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.

(Continued)

*Primary Examiner* — David M Upchurch
(74) *Attorney, Agent, or Firm* — Knobbe, Martens, Olson & Bear, LLP

(57) ABSTRACT

A directional lock or a headgear or interface assembly comprising one or more directional locks that include a catch arrangement for initiating or assisting in movement of a lock member of the direction lock. In some configurations, the catch arrangement assists movement of the lock member in only a portion of a range of travel of the lock member. In some configurations, the directional lock comprises a housing and a sleeve and the catch arrangement comprises a catch arm carried by the sleeve. The catch arm includes a catch end that contacts the lock member, which can be a lock washer in some configurations.

19 Claims, 24 Drawing Sheets

Related U.S. Application Data

(60) Provisional application No. 62/343,711, filed on May 31, 2016, provisional application No. 62/309,394, filed on Mar. 16, 2016.

(51) Int. Cl.

| | |
|---|---|
| *F16B 2/08* | (2006.01) |
| *F16B 2/06* | (2006.01) |
| *A42B 3/04* | (2006.01) |
| *A01K 1/06* | (2006.01) |
| *B68B 5/06* | (2006.01) |
| *E05B 69/00* | (2006.01) |
| *A61F 5/37* | (2006.01) |
| *A42B 1/04* | (2021.01) |
| *A42B 1/02* | (2006.01) |
| *F16B 2/18* | (2006.01) |
| *A62B 18/08* | (2006.01) |

(52) U.S. Cl.
CPC ............. *A42B 1/04* (2013.01); *A42B 3/0406* (2013.01); *A61F 5/3707* (2013.01); *A61M 16/0605* (2014.02); *B68B 5/06* (2013.01); *E05B 69/00* (2013.01); *F16B 2/06* (2013.01); *F16B 2/08* (2013.01); *F16G 11/10* (2013.01); *F16G 11/101* (2013.01); *F16G 11/105* (2013.01); *F16G 11/108* (2013.01); *A62B 18/084* (2013.01); *F16G 11/106* (2013.01)

(58) Field of Classification Search
CPC ....... A42B 3/0406; A61F 5/3707; B68B 5/06; E05B 69/00; F16B 2/16; F16B 2/18; F16G 11/10; F16G 11/101; F16G 11/105; F16G 11/108; F16G 11/106; A62B 18/084
See application file for complete search history.

(56) References Cited

U.S. PATENT DOCUMENTS

| | | | |
|---|---|---|---|
| 577,926 A | 3/1897 | Miller | |
| 718,470 A | 1/1903 | Jones | |
| 751,091 A | 2/1904 | Moran | |
| 770,013 A | 9/1904 | Linn | |
| 1,364,104 A | 1/1921 | Geer | |
| 1,635,545 A | 7/1927 | Drager | |
| 1,942,442 A | 1/1934 | Motsinger | |
| 2,199,690 A | 5/1940 | Bullard | |
| 2,296,150 A | 9/1942 | Dockson et al. | |
| 2,353,643 A | 7/1944 | Bulbulian | |
| 2,359,506 A | 10/1944 | Battley et al. | |
| 2,388,604 A | 11/1945 | Eisenbud | |
| 2,390,233 A | 12/1945 | Akerman et al. | |
| 2,508,050 A | 5/1950 | Valente | |
| 2,586,851 A | 2/1952 | Monro et al. | |
| 2,611,897 A | 9/1952 | Adams | |
| 2,661,514 A | 12/1953 | Ada | |
| 2,693,800 A | 11/1954 | Caldwell | |
| 2,738,788 A | 3/1956 | Matheson et al. | |
| 2,843,121 A | 7/1958 | Hudson | |
| 2,859,748 A | 11/1958 | Hudson | |
| 3,045,672 A | 7/1962 | Croasdaile | |
| 3,156,922 A | 11/1964 | Anderson | |
| 3,295,529 A | 1/1967 | Corrigall et al. | |
| 3,416,521 A | 12/1968 | Humphrey | |
| 3,457,564 A | 7/1969 | Holloway | |
| 3,490,452 A | 1/1970 | Greenfield | |
| 3,500,474 A | 3/1970 | Austin | |
| 3,530,031 A | 9/1970 | Loew | |
| 3,792,702 A | 2/1974 | Delest | |
| 3,834,682 A | 9/1974 | McPhee | |
| 3,850,171 A | 11/1974 | Ball et al. | |
| 3,887,968 A | 6/1975 | Lynam | |
| 3,972,321 A | 8/1976 | Proctor | |
| 3,990,757 A | 11/1976 | Gill | |
| 3,992,720 A | 11/1976 | Nicolinas | |
| 3,994,022 A | 11/1976 | Villari et al. | |
| 4,051,556 A | 10/1977 | Davenport et al. | |
| 4,062,068 A | 12/1977 | Davenport et al. | |
| 4,090,510 A | 5/1978 | Segersten | |
| D250,047 S | 10/1978 | Lewis et al. | |
| D250,131 S | 10/1978 | Lewis et al. | |
| 4,127,130 A | 11/1978 | Naysmith | |
| D252,322 S | 7/1979 | Johnson | |
| 4,167,185 A | 9/1979 | Lewis | |
| 4,201,205 A | 5/1980 | Bartholomew | |
| 4,266,540 A | 5/1981 | Panzik et al. | |
| 4,278,082 A | 7/1981 | Blackmer | |
| 4,288,891 A | 9/1981 | Boden | |
| 4,313,437 A | 2/1982 | Martin | |
| 4,328,605 A | 5/1982 | Hutchinson, V et al. | |
| 4,354,488 A | 10/1982 | Bartos | |
| 4,367,735 A | 1/1983 | Dali | |
| 4,402,316 A | 9/1983 | Gadberry | |
| 4,413,382 A | 11/1983 | Siegmann | |
| 4,437,462 A | 3/1984 | Piljay | |
| 4,453,292 A | 6/1984 | Bakker | |
| 4,458,373 A | 7/1984 | Maslow | |
| 4,477,928 A | 10/1984 | Graff | |
| 4,606,077 A | 8/1986 | Phillips | |
| D293,613 S | 1/1988 | Wingler | |
| 4,734,940 A | 4/1988 | Galet et al. | |
| 4,753,233 A | 6/1988 | Grimes | |
| 4,782,832 A | 11/1988 | Trimble et al. | |
| 4,817,596 A | 4/1989 | Gallet | |
| 4,848,334 A | 7/1989 | Bellm | |
| 4,853,275 A | 8/1989 | Tracy et al. | |
| 4,856,508 A | 8/1989 | Tayebi | |
| 4,915,105 A | 4/1990 | Lee | |
| 4,941,467 A | 7/1990 | Takata | |
| 4,944,310 A | 7/1990 | Sullivan | |
| 4,947,488 A | 8/1990 | Ashinoff | |
| D310,431 S | 9/1990 | Bellm | |
| 4,971,051 A | 11/1990 | Toffolon | |
| 4,986,269 A | 1/1991 | Hakkinen | |
| 5,010,925 A | 4/1991 | Atkinson et al. | |
| 5,016,625 A | 5/1991 | Hsu et al. | |
| 5,042,478 A | 8/1991 | Kopala et al. | |
| D320,677 S | 10/1991 | Kumagai et al. | |
| 5,052,084 A | 10/1991 | Braun | |
| D321,419 S | 11/1991 | Wallace | |
| 5,065,756 A | 11/1991 | Rapoport | |
| 5,074,297 A | 12/1991 | Venegas | |
| 5,094,236 A | 3/1992 | Tayebi | |
| 5,113,857 A | 5/1992 | Dickerman et al. | |
| 5,148,578 A * | 9/1992 | Clarke | A41F 17/00 24/41.1 |
| 5,148,802 A | 9/1992 | Sanders et al. | |
| 5,191,882 A | 3/1993 | Vogliano | |
| 5,231,979 A | 8/1993 | Rose | |
| 5,245,995 A | 9/1993 | Sullivan et al. | |
| D340,317 S | 10/1993 | Cole | |
| 5,269,296 A | 12/1993 | Landis et al. | |
| D354,128 S | 1/1995 | Rinehart | |
| D355,484 S | 2/1995 | Rinehart | |
| 5,388,743 A | 2/1995 | Silagy | |
| 5,438,979 A | 8/1995 | Johnson et al. | |
| 5,477,852 A | 12/1995 | Landis et al. | |
| 5,488,948 A | 2/1996 | Dubruille | |
| 5,513,634 A | 5/1996 | Jackson | |
| 5,529,062 A | 6/1996 | Byrd | |
| 5,533,506 A | 7/1996 | Wood | |
| 5,546,605 A | 8/1996 | Mallardi | |
| 5,551,419 A | 9/1996 | Froehlich et al. | |
| 5,566,395 A | 10/1996 | Nebeker | |
| 5,595,174 A | 1/1997 | Gwaltney | |
| 5,601,078 A | 2/1997 | Schaller et al. | |
| D378,610 S | 3/1997 | Reischel et al. | |
| 5,657,752 A | 8/1997 | Landis et al. | |
| 5,724,965 A | 3/1998 | Handke et al. | |
| 5,752,510 A | 5/1998 | Goldstein | |
| 5,755,578 A | 5/1998 | Contant et al. | |

(56) References Cited

U.S. PATENT DOCUMENTS

| | | |
|---|---|---|
| 5,774,901 A | 7/1998 | Minami |
| 5,884,624 A | 3/1999 | Barnett et al. |
| 5,921,239 A | 7/1999 | McCall et al. |
| 5,941,245 A | 8/1999 | Hannah et al. |
| 5,941,856 A | 8/1999 | Kovacs et al. |
| 6,017,315 A | 1/2000 | Starr et al. |
| 6,019,101 A | 2/2000 | Cotner et al. |
| 6,044,844 A | 4/2000 | Kwok et al. |
| 6,050,260 A | 4/2000 | Daniell et al. |
| 6,119,694 A | 9/2000 | Correa et al. |
| 6,192,886 B1 | 2/2001 | Rudolph |
| D440,302 S | 4/2001 | Wolfe |
| 6,256,798 B1 | 7/2001 | Egolf et al. |
| 6,272,690 B1 | 8/2001 | Carey et al. |
| 6,282,725 B1 | 9/2001 | Vanidestine, Jr. |
| 6,298,850 B1 | 10/2001 | Argraves |
| 6,338,342 B1 | 1/2002 | Fecteau et al. |
| 6,347,631 B1 | 2/2002 | Hansen et al. |
| D455,891 S | 4/2002 | Biedrzycki |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,470,886 B1 | 10/2002 | Jestrabek-Hart |
| 6,478,026 B1 | 11/2002 | Wood |
| 6,491,034 B1 | 12/2002 | Gunaratnam et al. |
| 6,536,435 B1 | 3/2003 | Fecteau et al. |
| 6,561,188 B1 | 5/2003 | Ellis |
| 6,561,191 B1 | 5/2003 | Kwok |
| 6,581,594 B1 | 6/2003 | Drew et al. |
| 6,581,601 B2 | 6/2003 | Ziaee |
| 6,588,424 B2 | 7/2003 | Bardel |
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,659,102 B1 | 12/2003 | Sico |
| 6,662,803 B2 | 12/2003 | Gradon et al. |
| 6,679,257 B1 | 1/2004 | Robertson et al. |
| 6,679,265 B2 | 1/2004 | Strickland et al. |
| 6,772,761 B1 | 8/2004 | Rucker, Jr. |
| 6,851,425 B2 | 2/2005 | Jaffre et al. |
| 6,883,519 B2 | 4/2005 | Schmidtke et al. |
| 6,886,564 B2 | 5/2005 | Sullivan et al. |
| 6,892,729 B2 | 5/2005 | Smith et al. |
| 6,907,882 B2 | 6/2005 | Ging et al. |
| 6,951,218 B2 | 10/2005 | Gradon et al. |
| 7,004,165 B1 | 2/2006 | Salcido |
| D520,140 S | 5/2006 | Chaggares |
| 7,036,508 B2 | 5/2006 | Kwok |
| 7,062,795 B2 | 6/2006 | Skiba et al. |
| 7,066,179 B2 | 6/2006 | Eaton et al. |
| D526,094 S | 8/2006 | Chen |
| 7,096,864 B1 | 8/2006 | Mayer et al. |
| 7,096,867 B2 | 8/2006 | Smith et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,318,437 B2 | 1/2008 | Gunaratnam et al. |
| 7,353,826 B2 | 4/2008 | Sleeper et al. |
| 7,353,827 B2 | 4/2008 | Geist |
| 7,814,911 B2 | 10/2010 | Bordewick et al. |
| 7,845,352 B2 | 12/2010 | Sleeper et al. |
| 7,861,715 B2 | 1/2011 | Jones et al. |
| 7,870,860 B2 | 1/2011 | McCormick et al. |
| 7,896,003 B2 | 3/2011 | Matula et al. |
| 7,913,692 B2 | 3/2011 | Kwok |
| 7,967,014 B2 | 6/2011 | Heidmann |
| 8,042,539 B2 | 10/2011 | Chandran et al. |
| 8,047,893 B2 | 11/2011 | Fenske |
| 8,074,651 B2 | 12/2011 | Bierman et al. |
| 8,104,473 B2 | 1/2012 | Woodard et al. |
| 8,132,270 B2 | 3/2012 | Lang et al. |
| 8,136,524 B2 | 3/2012 | Ging et al. |
| 8,297,285 B2 | 10/2012 | Henry et al. |
| 8,371,302 B2 | 2/2013 | Ging et al. |
| 8,443,807 B2 | 5/2013 | McAuley et al. |
| D686,313 S | 7/2013 | Matula et al. |
| 8,479,741 B2 | 7/2013 | McAuley et al. |
| 8,505,538 B2 | 8/2013 | Amarasinghe |
| 8,522,785 B2 | 9/2013 | Berthon-Jones et al. |
| 8,573,201 B2 | 11/2013 | Rummery et al. |
| 8,596,271 B2 | 12/2013 | Matula, Jr. et al. |
| 8,596,274 B2 | 12/2013 | Hieber et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,636,008 B2 | 1/2014 | Flory et al. |
| 8,757,157 B2 | 6/2014 | Price et al. |
| 8,783,257 B2 | 7/2014 | McAuley et al. |
| 8,794,239 B2 | 8/2014 | Gunaratnam |
| 8,857,435 B2 | 10/2014 | Matula, Jr. et al. |
| 8,915,251 B2 | 12/2014 | Lubke et al. |
| 8,997,742 B2 | 4/2015 | Moore et al. |
| 9,032,955 B2 | 5/2015 | Lubke et al. |
| 9,044,564 B2 | 6/2015 | Dravitzki et al. |
| 9,138,555 B2 | 9/2015 | McAuley et al. |
| 9,149,596 B2 | 10/2015 | Valcic et al. |
| 9,265,909 B2 | 2/2016 | Ho et al. |
| 9,302,065 B2 | 4/2016 | Smith et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,480,809 B2 | 11/2016 | Guney et al. |
| 9,517,320 B2 | 12/2016 | Barlow et al. |
| 9,550,038 B2 | 1/2017 | McAuley et al. |
| 9,592,336 B2 | 3/2017 | Nielsen et al. |
| 9,656,038 B2 | 5/2017 | Rummery et al. |
| 9,744,385 B2 | 8/2017 | Henry |
| 9,782,554 B2 | 10/2017 | Mazzone et al. |
| 9,878,118 B2 | 1/2018 | Formica |
| D810,277 S | 2/2018 | Amarasinghe |
| 9,884,160 B2 | 2/2018 | Mcauley |
| 9,901,700 B2 | 2/2018 | McAuley et al. |
| 9,925,349 B2 | 3/2018 | Jablonski |
| 9,974,914 B2 | 5/2018 | McAuley |
| 9,993,606 B2 | 6/2018 | Gibson et al. |
| 10,039,665 B2 | 8/2018 | Blaszczykiewicz et al. |
| 10,065,010 B2 | 9/2018 | Smith et al. |
| 10,071,217 B2 | 9/2018 | Grashow |
| 10,080,856 B2 | 9/2018 | McLaren |
| 10,207,072 B2 | 2/2019 | Dunn et al. |
| 10,279,138 B2 | 5/2019 | Ovzinsky |
| 10,456,546 B2 | 10/2019 | McLaren et al. |
| 10,646,680 B2 | 5/2020 | Huddart et al. |
| 10,675,428 B2 | 6/2020 | Guney et al. |
| 10,792,451 B2 | 10/2020 | Allan et al. |
| 10,828,449 B2 | 11/2020 | Higgins et al. |
| 10,828,452 B2 | 11/2020 | Huddart et al. |
| 10,874,814 B2 | 12/2020 | Huddart et al. |
| 11,000,663 B2 | 5/2021 | Felix et al. |
| 11,331,449 B2 | 5/2022 | McLaren et al. |
| 11,607,518 B2 | 3/2023 | Hammer et al. |
| 2002/0005198 A1 | 1/2002 | Kwok et al. |
| 2002/0020416 A1 | 2/2002 | Namey |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0096178 A1 | 7/2002 | Ziaee |
| 2002/0157668 A1 | 10/2002 | Bardel |
| 2003/0005933 A1 | 1/2003 | Izuchukwu |
| 2003/0051732 A1 | 3/2003 | Smith et al. |
| 2003/0079749 A1 | 5/2003 | Strickland et al. |
| 2003/0084903 A1 | 5/2003 | Fecteau et al. |
| 2003/0111080 A1 | 6/2003 | Olsen et al. |
| 2003/0121519 A1 | 7/2003 | Estes et al. |
| 2003/0164170 A1 | 9/2003 | Drew et al. |
| 2003/0172936 A1 | 9/2003 | Wilkie et al. |
| 2003/0196656 A1 | 10/2003 | Moore |
| 2003/0196659 A1 | 10/2003 | Gradon et al. |

(56) References Cited

U.S. PATENT DOCUMENTS

| | | |
|---|---|---|
| 2003/0196664 A1 | 10/2003 | Jacobson |
| 2003/0200970 A1 | 10/2003 | Stenzler et al. |
| 2004/0067333 A1 | 4/2004 | Amarasinghe |
| 2004/0211427 A1 | 10/2004 | Jones et al. |
| 2004/0226566 A1 | 11/2004 | Gunaratnam et al. |
| 2005/0011524 A1 | 1/2005 | Thomlinson et al. |
| 2005/0016067 A1* | 1/2005 | Pettit ............... E05C 9/041 49/185 |
| 2005/0028822 A1 | 2/2005 | Sleeper et al. |
| 2005/0033247 A1 | 2/2005 | Thompson |
| 2005/0066976 A1 | 3/2005 | Wondka |
| 2005/0076913 A1 | 4/2005 | Ho et al. |
| 2005/0098183 A1 | 5/2005 | Nash et al. |
| 2005/0150497 A1 | 7/2005 | Eifler et al. |
| 2005/0161049 A1 | 7/2005 | Wright |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2006/0060200 A1 | 3/2006 | Ho et al. |
| 2006/0081250 A1 | 4/2006 | Bordewick et al. |
| 2006/0096596 A1 | 5/2006 | Occhialini et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0137690 A1 | 6/2006 | Gunaratnam et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reier et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1* | 3/2008 | Fiser ............... A61M 25/0618 604/110 |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1 | 9/2008 | Valcic et al. |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2011/0048425 A1 | 3/2011 | Chang |
| 2011/0197341 A1 | 8/2011 | Formica |
| 2011/0220113 A1 | 9/2011 | Newman |
| 2011/0247628 A1 | 10/2011 | Ho |
| 2011/0259335 A1 | 10/2011 | Sullivan |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0304999 A1 | 12/2012 | Swift et al. |
| 2013/0000648 A1 | 1/2013 | Madaus et al. |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1 | 8/2013 | Barlow et al. |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0216452 A1 | 8/2014 | Miller et al. |
| 2014/0305439 A1 | 10/2014 | Chodkowski |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0082214 A1 | 3/2016 | Barlow et al. |
| 2016/0166793 A1 | 6/2016 | McLaren et al. |
| 2016/0178027 A1 | 6/2016 | Wetzel |
| 2016/0278463 A1 | 9/2016 | Stevenson |
| 2016/0375214 A1 | 12/2016 | Chodkowski et al. |
| 2017/0136269 A1 | 5/2017 | Jacotey et al. |
| 2017/0182276 A1 | 6/2017 | Hammer |
| 2017/0189636 A1 | 7/2017 | Gibson et al. |
| 2017/0216548 A1 | 8/2017 | Gerhardt |
| 2018/0214655 A1 | 8/2018 | Kooij et al. |
| 2018/0264218 A1 | 9/2018 | Chodkowski |

(56) References Cited

U.S. PATENT DOCUMENTS

| | | |
|---|---|---|
| 2018/0339123 A1 | 11/2018 | Smith et al. |
| 2019/0111227 A1 | 4/2019 | Veliss et al. |
| 2019/0151592 A1 | 5/2019 | Bornholdt |
| 2020/0129720 A1 | 4/2020 | McLaren et al. |
| 2020/0230343 A1 | 7/2020 | Sims et al. |
| 2020/0230344 A1 | 7/2020 | Huddart et al. |
| 2020/0338294 A1 | 10/2020 | McLaren et al. |
| 2021/0008316 A1 | 1/2021 | McLaren et al. |
| 2021/0016041 A1 | 1/2021 | Huddart et al. |
| 2022/0126049 A1 | 4/2022 | Amarasinghe |
| 2022/0331542 A1 | 10/2022 | McLaren et al. |

FOREIGN PATENT DOCUMENTS

| | | |
|---|---|---|
| CN | 2172538 | 7/1994 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 202822396 U | 3/2013 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 130 563 | 12/2009 |
| EP | 2 327 443 | 6/2011 |
| EP | 2 517 757 | 10/2012 |
| EP | 2 022 528 | 3/2016 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/038918 | 3/2009 |
| WO | WO 09/052560 | 4/2009 |
| WO | WO 09/059353 | 5/2009 |
| WO | WO 09/092057 | 7/2009 |
| WO | WO 09/108994 | 9/2009 |
| WO | WO 09/108995 | 9/2009 |
| WO | WO 09/139647 | 11/2009 |
| WO | WO 09/148956 | 12/2009 |
| WO | WO 10/066004 | 6/2010 |
| WO | WO 10/131189 | 11/2010 |
| WO | WO 10/139014 | 12/2010 |
| WO | WO 11/072739 | 6/2011 |
| WO | WO 11/077254 | 6/2011 |
| WO | WO 11/112401 | 9/2011 |
| WO | WO 12/07300 | 1/2012 |
| WO | WO 12/045127 | 4/2012 |
| WO | WO 12/069951 | 5/2012 |
| WO | WO 12/071300 | 5/2012 |
| WO | WO 12/143822 | 10/2012 |
| WO | WO 12/177152 | 12/2012 |
| WO | WO 13/006913 | 1/2013 |
| WO | WO 13/026091 | 2/2013 |
| WO | WO 13/026092 | 2/2013 |
| WO | WO 13/064930 | 5/2013 |
| WO | WO 14/020469 | 2/2014 |
| WO | WO 14/025267 | 2/2014 |
| WO | WO 14/031673 | 2/2014 |
| WO | WO 14/075141 | 5/2014 |
| WO | WO 14/077708 | 5/2014 |
| WO | WO 14/110622 | 7/2014 |
| WO | WO 14/110626 | 7/2014 |
| WO | WO 14/129913 | 8/2014 |
| WO | WO 14/175752 | 10/2014 |
| WO | WO 14/175753 | 10/2014 |
| WO | WO 15/033287 | 3/2015 |
| WO | WO 15/043229 | 4/2015 |
| WO | WO 15/070289 | 5/2015 |
| WO | WO 15/079396 | 6/2015 |
| WO | WO 15/083060 | 6/2015 |
| WO | WO 15/151019 | 10/2015 |
| WO | WO 15/187986 | 12/2015 |
| WO | WO 16/043603 | 3/2016 |
| WO | WO 17/030447 | 2/2017 |
| WO | WO 17/150990 | 9/2017 |
| WO | WO 17/158474 | 9/2017 |
| WO | WO 17/158544 | 9/2017 |
| WO | WO 17/160166 | 9/2017 |

(56) References Cited

FOREIGN PATENT DOCUMENTS

| WO | WO 17/216708 | 12/2017 |
|---|---|---|
| WO | WO 19/003094 | 1/2019 |

OTHER PUBLICATIONS

Pas A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.
Philips Respironics 'System One Heated Humidifier—User Manual', 2011, pp. 1-16, [retrieved on Nov. 25, 2013] from the internet: URL: http://www.cpapexhange.com/cpap-machines-biap-machines/system-one-60-series-cpap-humidifier-manual.pdf.

* cited by examiner

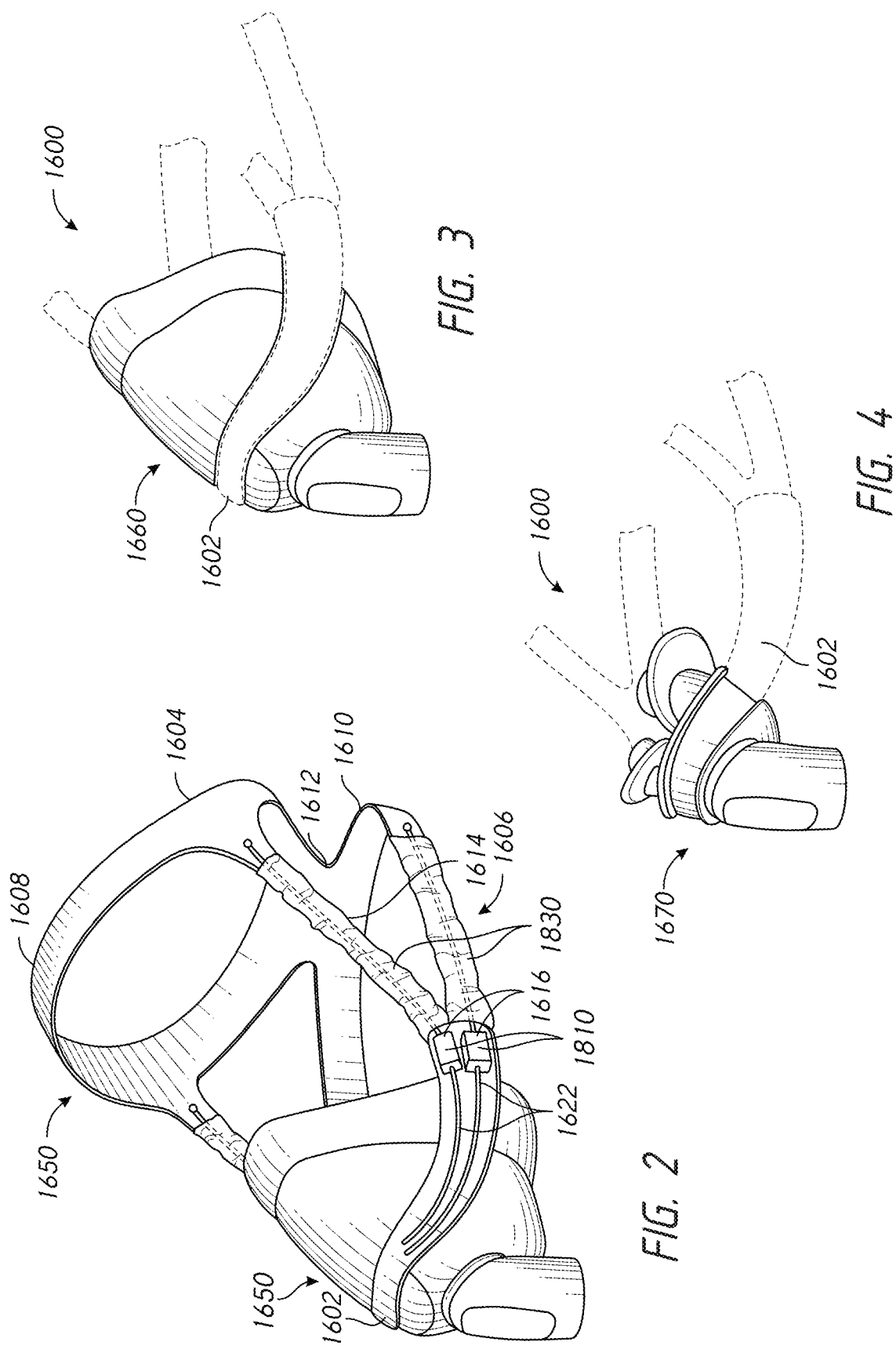

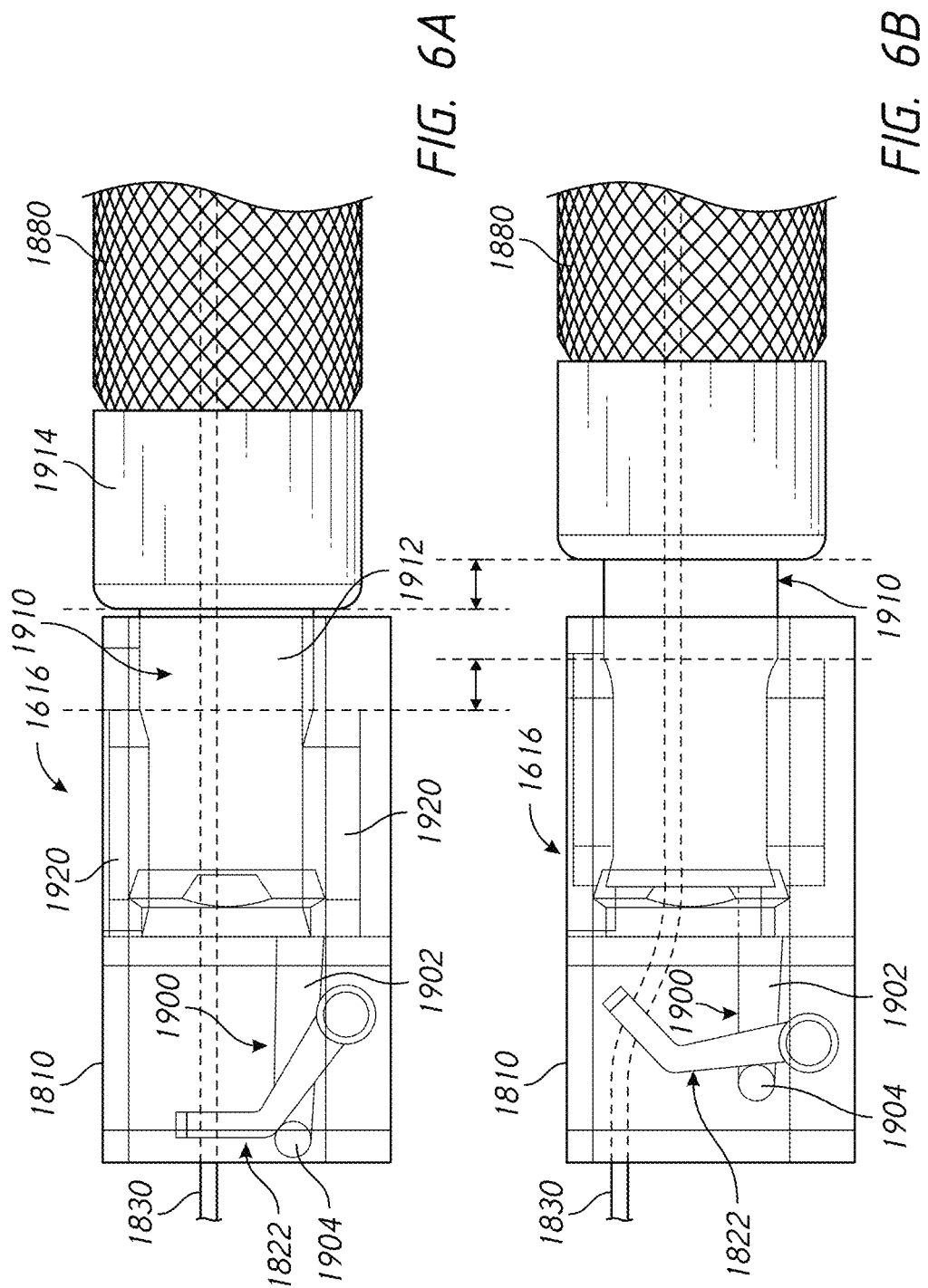

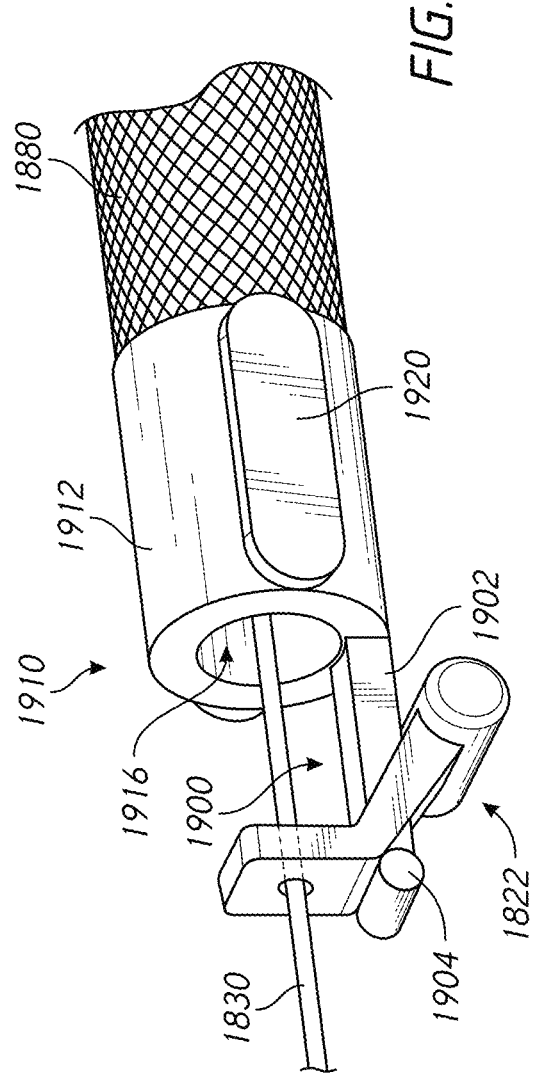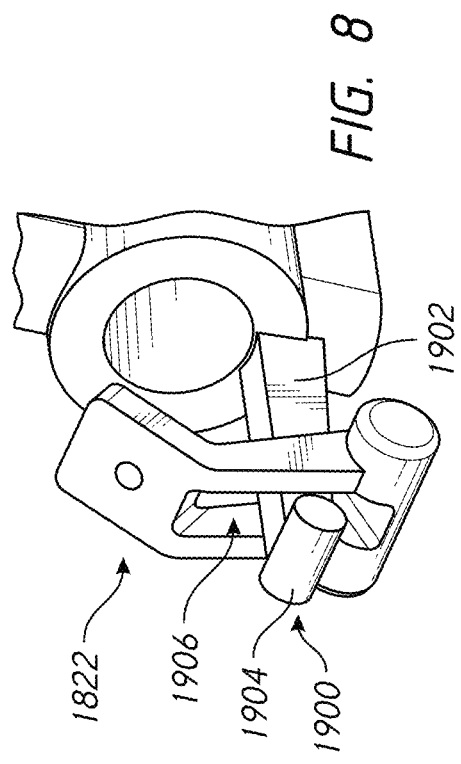

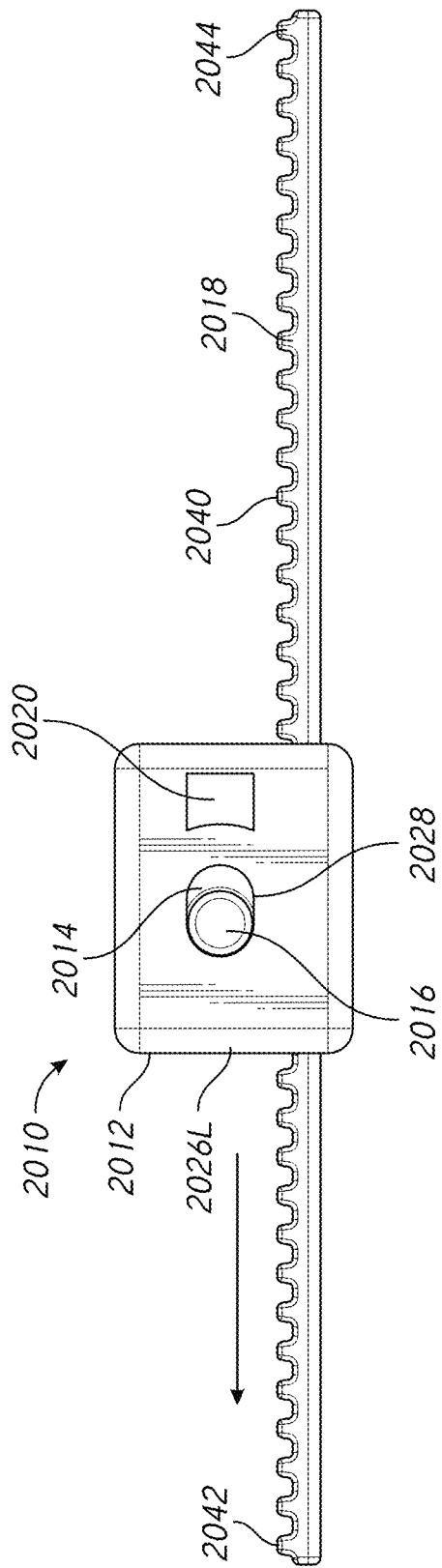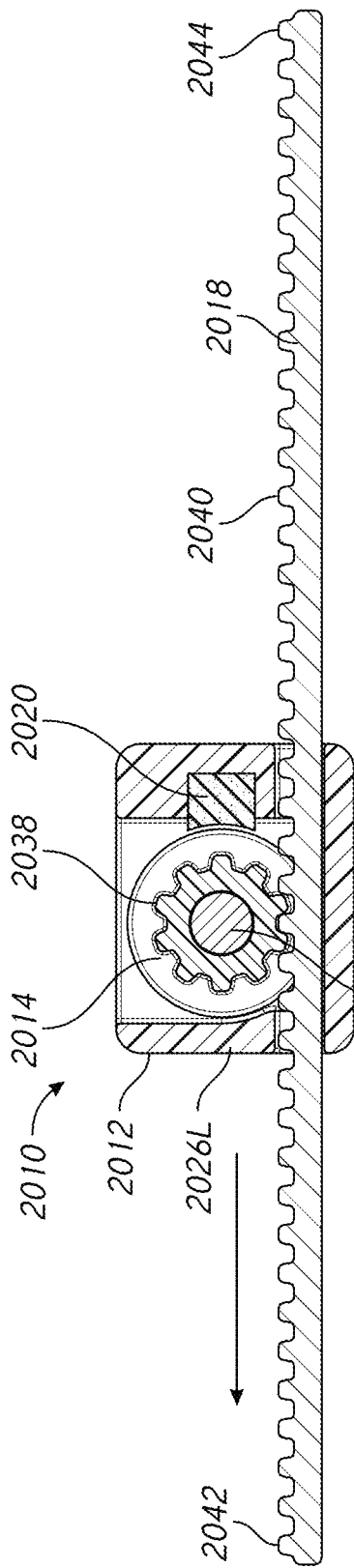

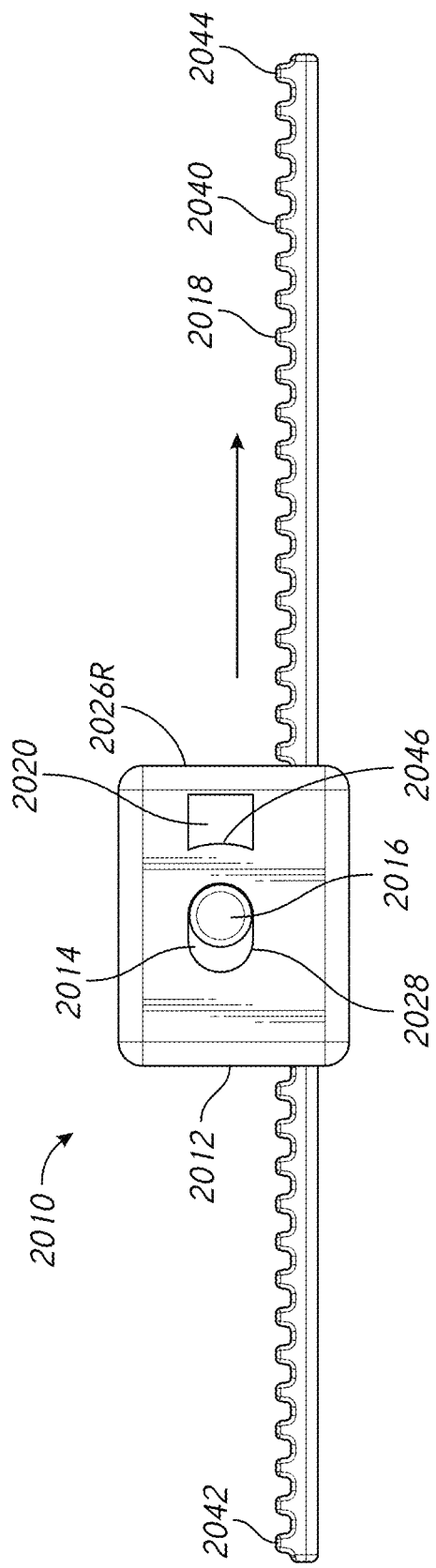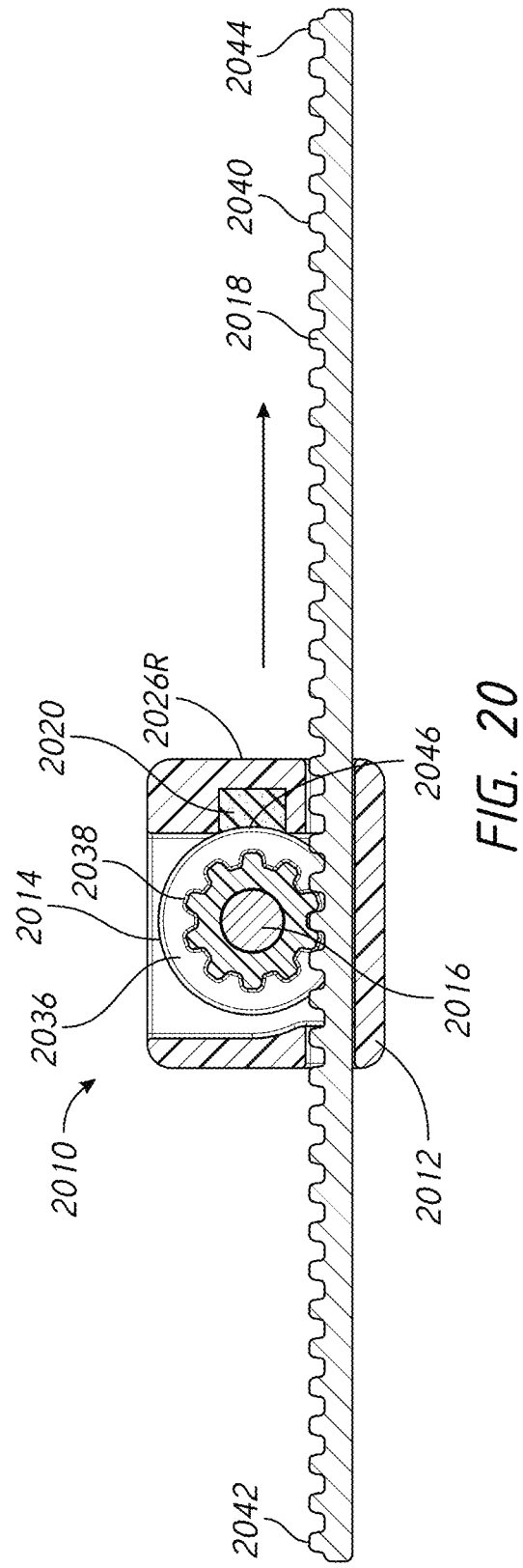

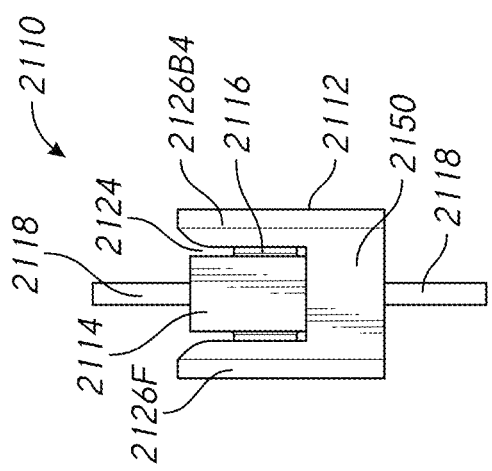
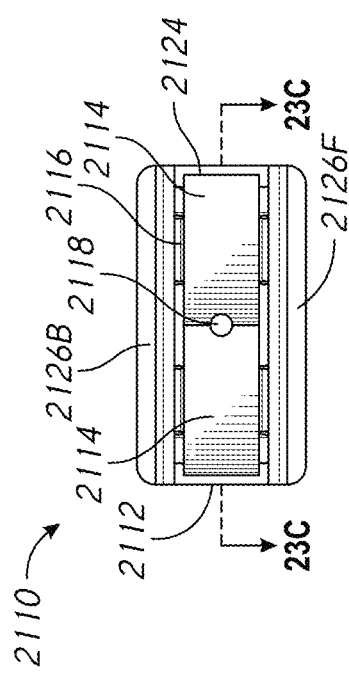
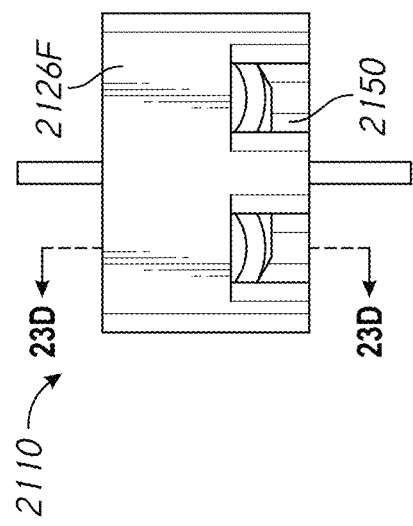
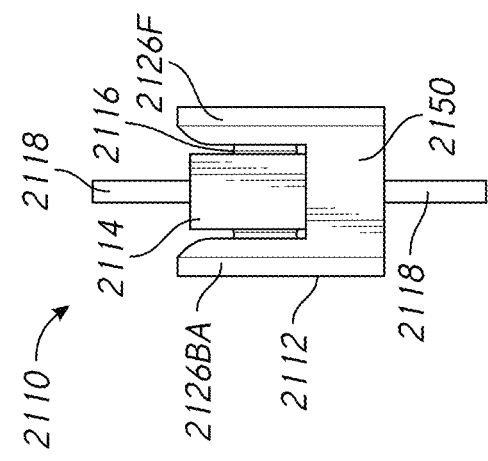
FIG. 22A FIG. 22B FIG. 22C FIG. 22D FIG. 22E

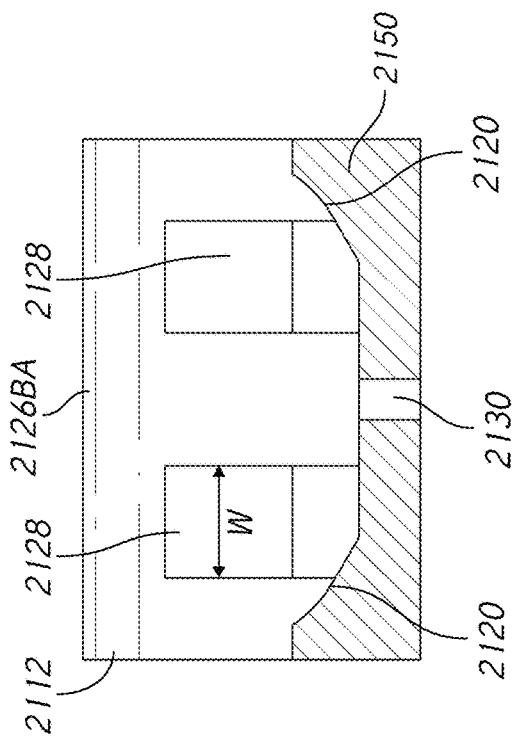
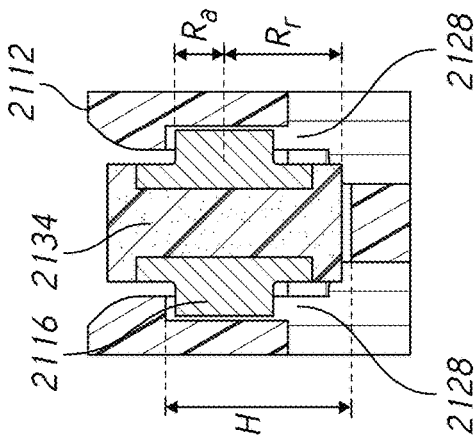
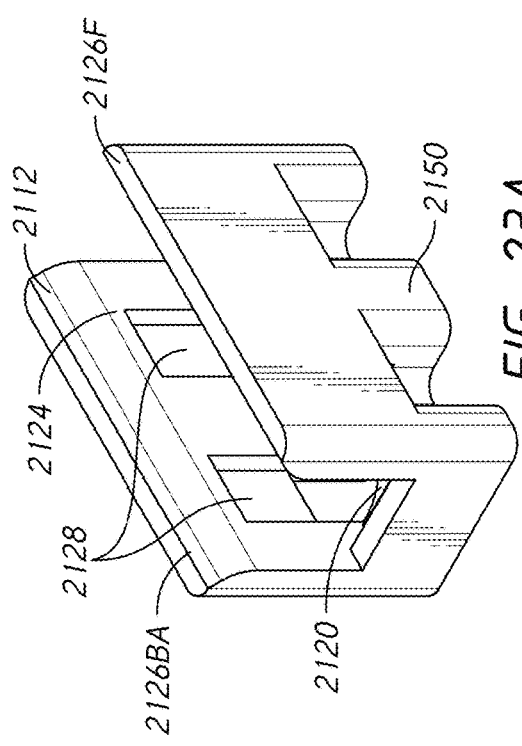
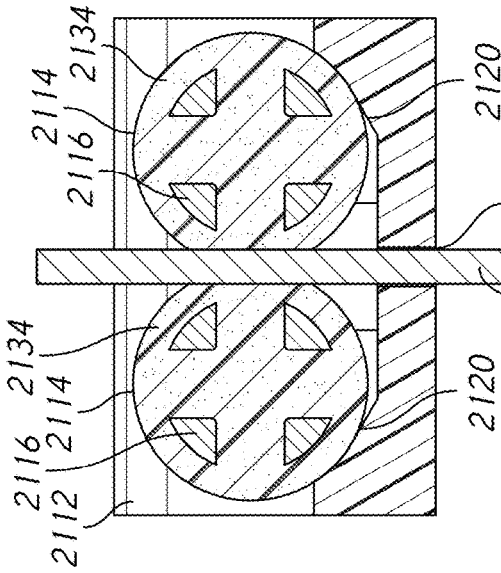
FIG. 23A
FIG. 23B
FIG. 23C
FIG. 23D

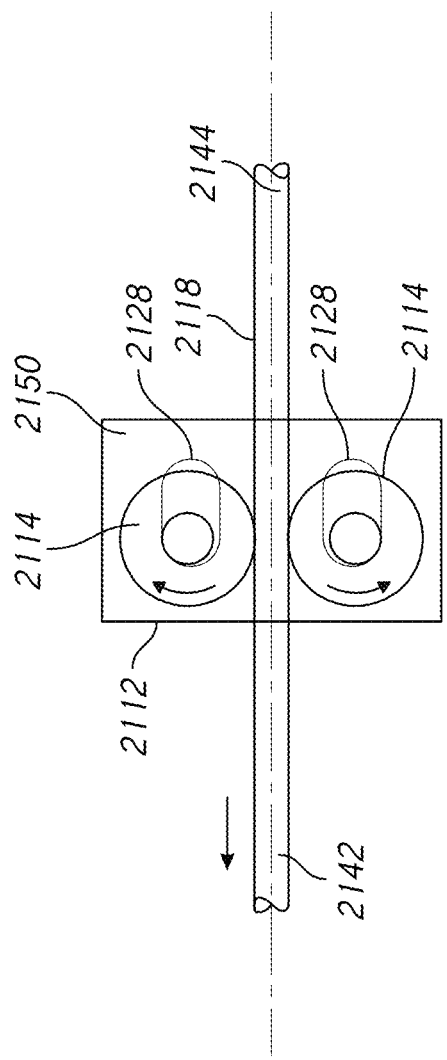

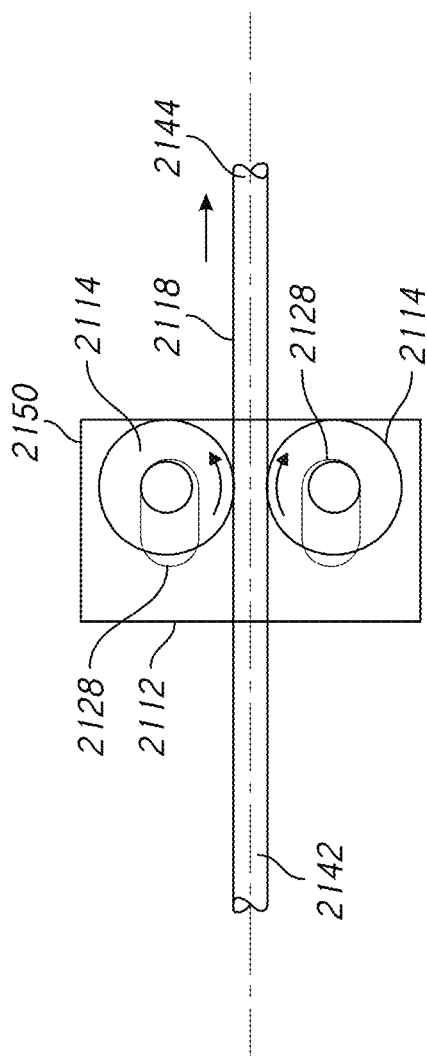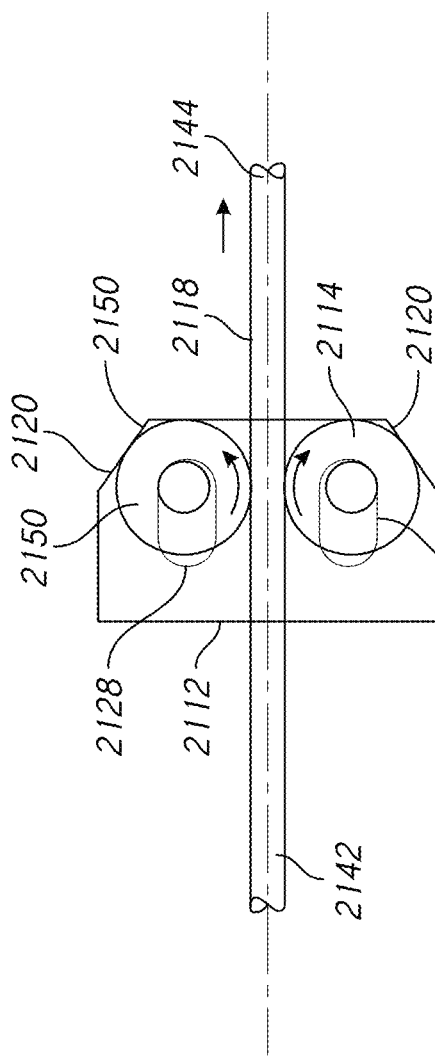

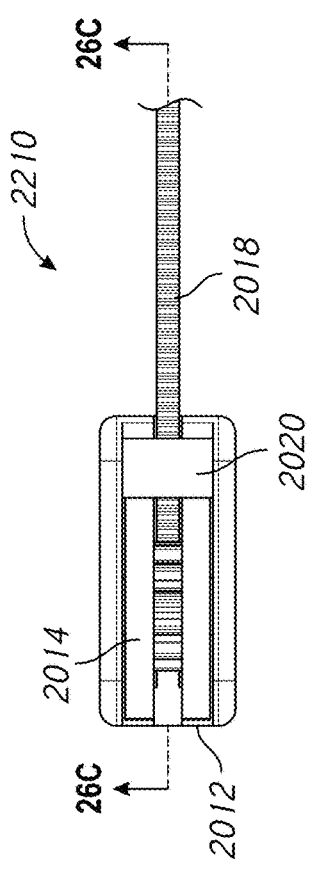
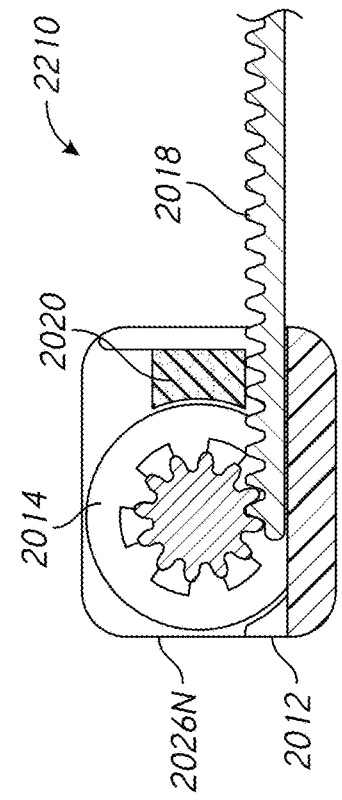
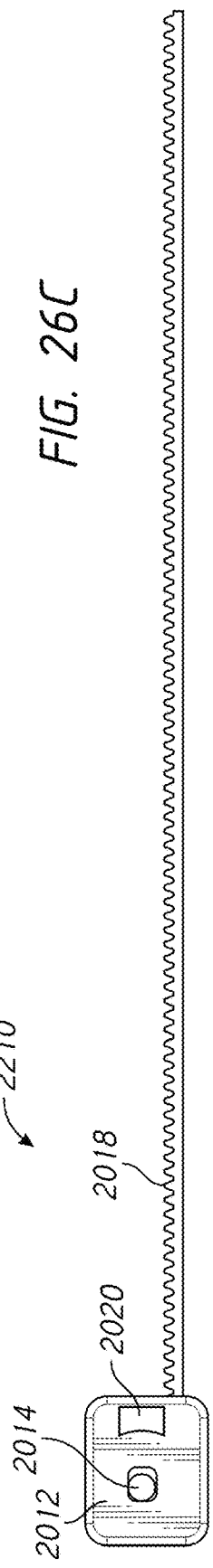
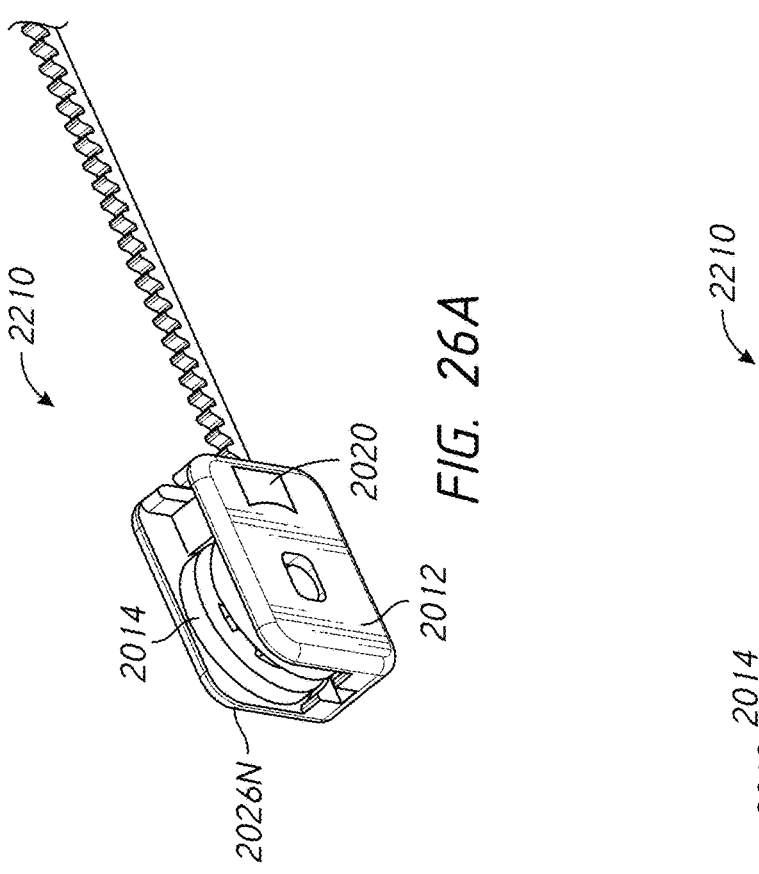
FIG. 26A
FIG. 26B
FIG. 26C
FIG. 26D

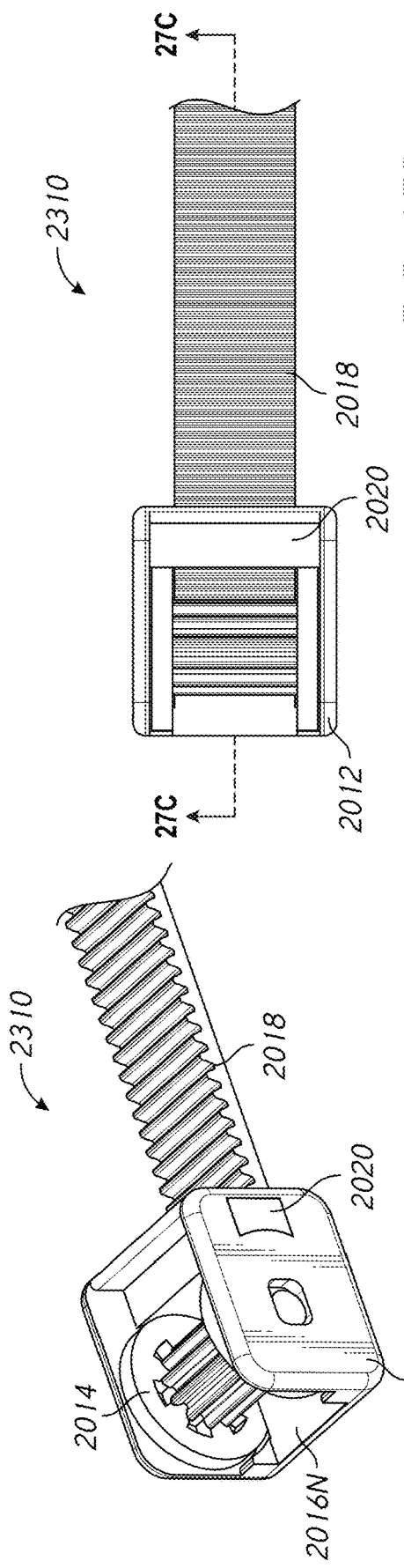
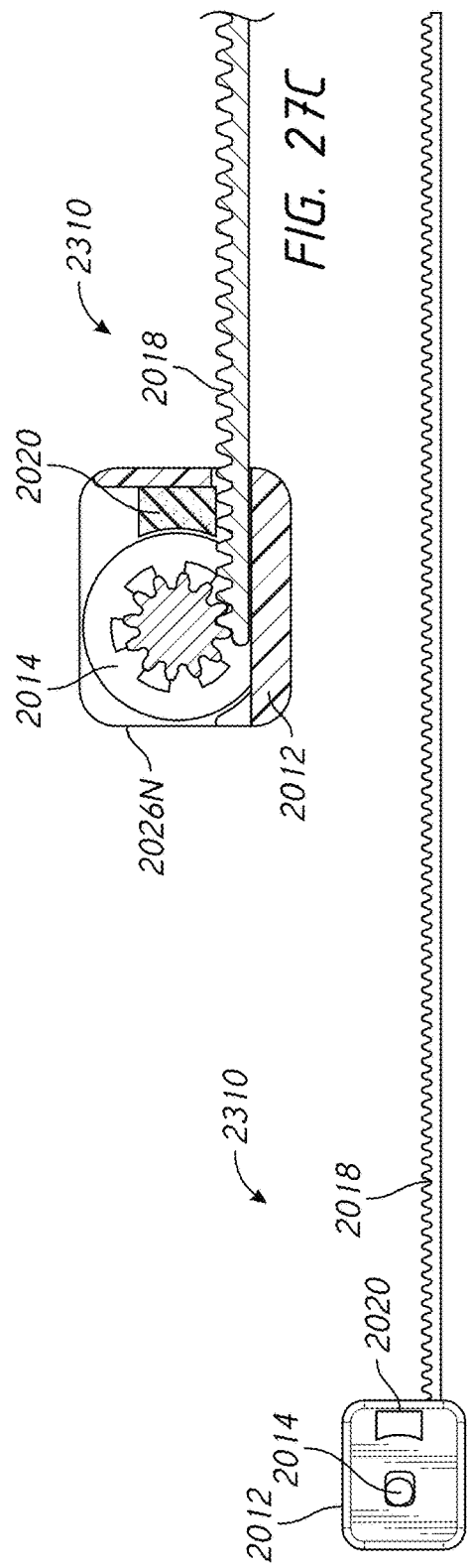
FIG. 27A
FIG. 27B
FIG. 27C
FIG. 27D

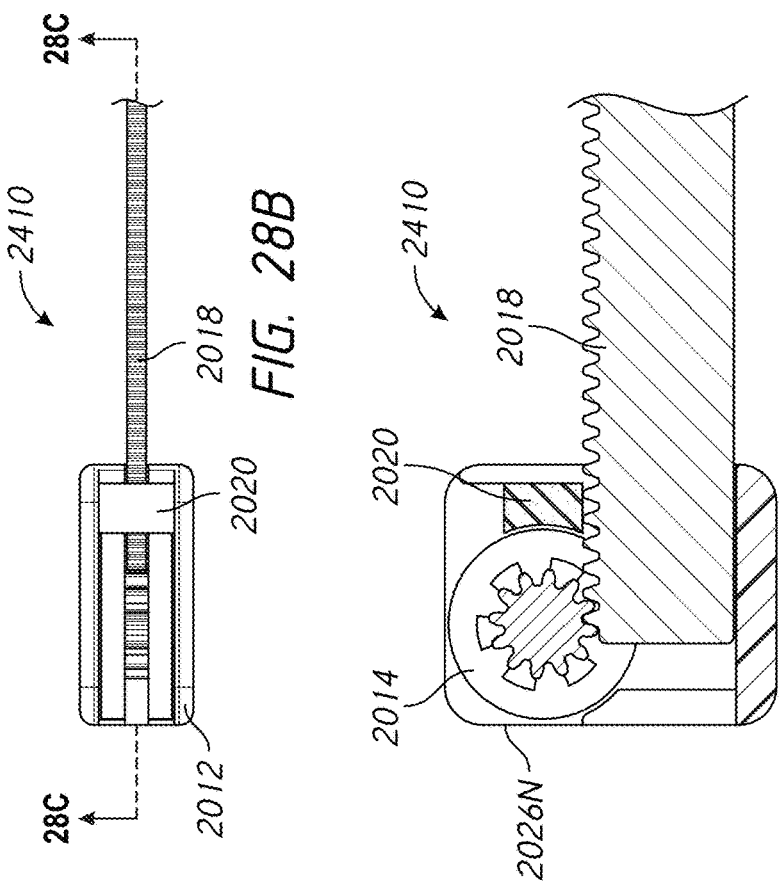
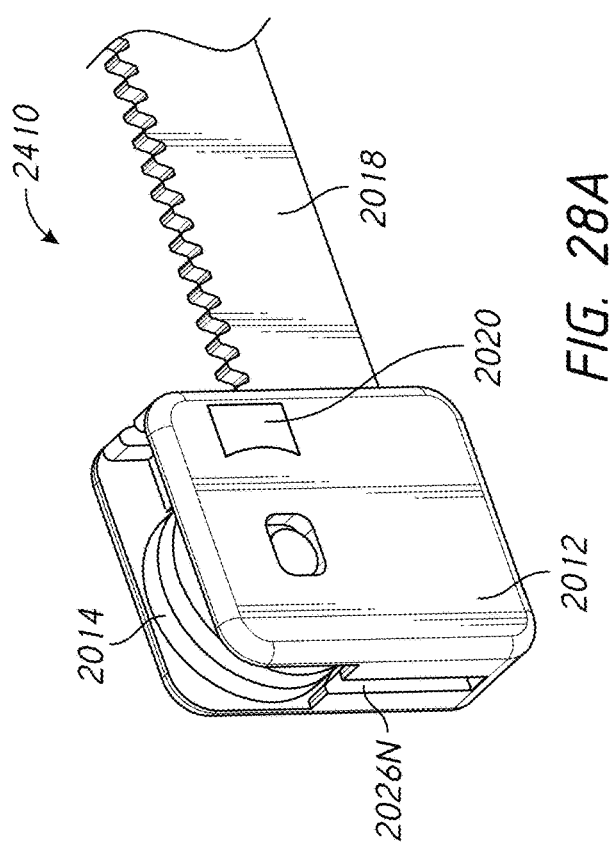
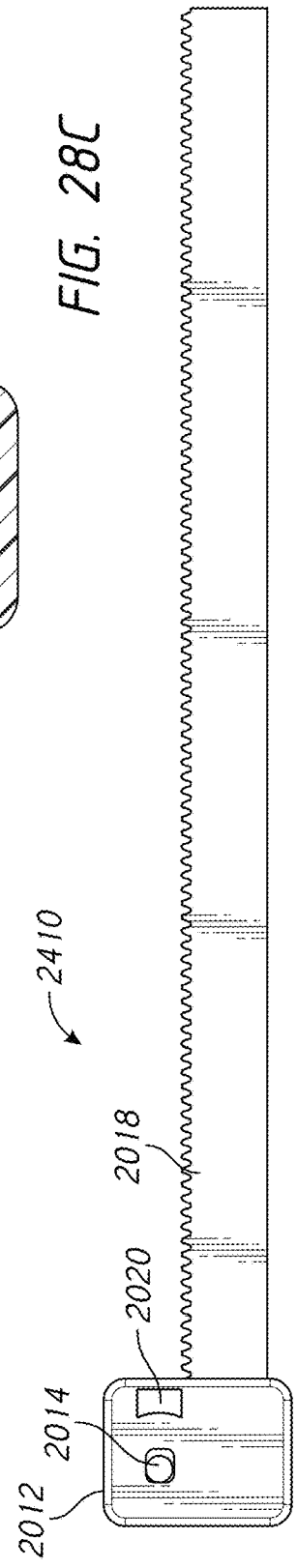
FIG. 28A
FIG. 28B
FIG. 28C
FIG. 28D

DIRECTIONAL LOCK FOR INTERFACE HEADGEAR ARRANGEMENT

INCORPORATION BY REFERENCE TO PRIORITY APPLICATIONS

This application is a continuation application of U.S. patent application Ser. No. 16/085,291, filed Sep. 14, 2018, which is a national stage application under 35 U.S.C. § 371(c) of PCT Application No. PCT/IB2017/051522, filed Mar. 16, 2017, which is related to and claims priority from U.S. Provisional Patent Application No. 62/309,394, filed Mar. 16, 2016, and U.S. Provisional Patent Application No. 62/343,711, filed May 31, 2016, the entireties of which are hereby incorporated by reference herein and made a part of the present disclosure.

BACKGROUND

Field

The present disclosure relates to respiratory therapy systems. In particular, the disclosure relates to interface assemblies for use in respiratory therapy and portions thereof.

Description of Related Art

The treatment of respiratory ailments or conditions with therapies such as non-invasive ventilation (NIV), Bi-level or continuous positive airway pressure (CPAP) therapy involves the delivery of pressurized air to the airways of a human via a conduit and an interface (e.g., a mask). Some types of interfaces create at least a substantial "seal" on or around the nose and/or the mouth of the user.

The result of creating this "seal" is that the combination of the enclosure area of the interface and its internal pressure creates a resulting force (a "blow off" force) that attempts to push the mask off the face. To restrain this force it is normal to use a headgear arrangement having one or more straps that pass around the back of the head.

The strap(s) require some form of adjustment to account for variation in head size, this adjustment mechanism is typically provided via an adjustment loop between the mask body and the head gear. The adjustment loop can have a hook-and-loop or similar fastener that permits an end of the strap to be passed through a mounting location on the mask or through a clip that attaches to the mask and then attached to another section of the strap. Such an arrangement permits adjustment of the headgear by positioning the end of the strap at a desired location on the other section of the strap to vary a size of the adjustment loop.

These types of mechanism are one solution to providing an adjustment mechanism for the headgear and, thus, the interface assembly. Such systems also require a reasonable level of user interaction and, as a result, is prone to misuse or mis-adjustment (e.g., over-tightening). As a practical matter, micro-adjustment of such systems is difficult and time-consuming to accomplish. The creation of practical and not so practical solutions to this has been the subject of considerable development effort from a number of organisations, which has resulted in numerous patents.

SUMMARY

The systems, methods and devices described herein have innovative aspects, no single one of which is indispensable or solely responsible for their desirable attributes. Without limiting the scope of the claims, some of the advantageous features will now be summarized.

In some configurations, a directional lock includes a housing defining an interior space, a first opening and a second opening. Each of the first and second openings communicates with the interior space. A sleeve is movably coupled to the housing and includes a catch element. The sleeve is displaceable between a first displacement position and a second displacement position. At least one lock element is disposed within the housing. The lock element has a first aperture configured to receive a core element and a second aperture to cooperate with the catch element. The lock element is movable between a first position, in which the aperture is aligned with the first opening and the second opening, and a second position, in which the aperture is not aligned with the first opening and the second opening. Displacement of the sleeve from the first displacement position to the second displacement position causes the catch element to at least assist or initiate movement of the lock element from the first position toward the second position at least to an intermediate position.

In some configurations, the lock element is a lock washer.

In some configurations, the lock element is pivotally coupled to the housing for rotation about a fixed pivot axis.

In some configurations, a pivot axis of the lock element is movable relative to the housing.

In some configurations, the sleeve is disposed within the housing.

In some configurations, the sleeve comprises a conduit portion through which the core can pass.

In some configurations, the catch element comprises a catch arm and a catch end.

In some configurations, the catch end of the catch element is round.

In some configurations, a surface of the catch end that contacts the lock element is non-planar.

In some configurations, the catch end is configured to catch or engage the lock element when the sleeve is displaced from the first displacement position to the second displacement position.

In some configurations, the catch arm is narrower in width than the second aperture of the lock element.

In some configurations, the catch end is wider in width than the second aperture of the lock element.

In some configurations, the sleeve includes at least one stop-guide.

In some configurations, the stop-guide is configured to engage the housing so as to stop displacement of the sleeve at the second displacement position.

In some configurations, the stop-guide is configured to engage the housing so as to stop displacement.

In some configurations, the stop-guide is positioned on the conduit portion.

In some configurations, the sleeve includes a cuff.

In some configurations, the sleeve is displaceable from the second displacement position to the first displacement position.

In some configurations, the sleeve is displaced from the first displacement position to the second displacement position during donning.

In some configurations, the housing includes a displacement slot.

In some configurations, the displacement slot is an elongate slot.

In some configurations, the displacement slot includes at least a first stop end.

In some configurations, the first stop end limits displacement of the sleeve.

In some configurations, the stop-guide abuts or engages the first stop end in the second displacement position.

In some configurations, the displacement slot includes a second stop.

In some configurations, a difference between the first displacement position and the second displacement position is a displacement distance.

In some configurations, the displacement distance is an initial displacement.

In some configurations, a distance between the first displacement position and the second displacement position is a linear distance.

In some configurations, the lock element is angularly movable.

In some configurations, the difference between the first position and the second position of the lock element is an angular distance or rotation.

In some configurations, linear displacement of the sleeve translates to angular movement of the lock element.

In some configurations, the difference between the first position and the second position of the lock element is a function of the difference between the first displacement position and the second displacement position.

In some configurations, the angular distance is a function of the displacement distance.

In some configurations, the intermediate position of the lock element is between the first and second positions.

In some configurations, the intermediate position is the same as the second position.

In some configurations, the lock element does not contact the catch element in the second position.

In some configurations, the lock element contacts the catch element in the second position.

In some configurations, the catch end moves along the elongate slot during displacement.

In some configurations, the catch end catches or pulls the lock element into activation with the core element.

In some configurations, the catch end catches or pushes the lock element into activation with the core element.

In some configurations, the catch end abuts the locking element during movement between the first position and the intermediate position.

In some configurations, a first difference between the first position and the intermediate position is less than a second difference between the intermediate position and the second position.

In some configurations, a ratio of second difference to first difference is 3:1.

In some configurations, a ratio of second difference to first difference is one of: 5:1, 4:1, 3:1, 2:1.

In some configurations, a ratio of second difference to first difference is one of: 2.1 to 3.9:1, or 1.1 to 4.9:1.

In some configurations, a ratio of second difference to first difference is one of: 1 to 5:1, 2 to 5:1, 3 to 5:1, 2 to 4:1, 1 to 4:1, 1 to 3:1.

In some configurations, a headgear assembly includes a directional lock according to any of the preceding claims, and a biasing element connected to the sleeve.

In some configurations, the sleeve is displaced from the first displacement position to the second displacement position during donning.

In some configurations, the sleeve is displaced during an initial extension of the biasing element.

In some configurations, the sleeve is displaced from the first displacement position to the second displacement position during an initial extension of the biasing element.

In some configurations, the sleeve is displaced from the second displacement position to the first displacement position when the biasing element retracts.

In some configurations, the sleeve is displaced from the second displacement position to the first displacement position when the biasing element is fully retracted.

In some configurations, a directional lock includes a core element, at least one lock element, the lock element having an aperture through which the core element passes, and a lock activator configured to activate, promote, or assist movement of the lock element.

In some configurations, the lock activator is configured to activate, promote or assist movement of the lock element during initial displacement or elongation of the headgear.

In some configurations, the lock activator is configured to activate prior to any elongation of the headgear.

In some configurations, a directional lock includes a housing, a rack and pinion mechanism and a brake. The housing has an interior space, a first opening and a second opening. Each of the first and second openings communicates with the interior space. The rack and pinion mechanism includes a pinion positioned within the interior space and rotatable relative to the housing. The pinion is configured to move between a first displacement position and a second displacement position. The rack and pinion mechanism includes a rack engaged with the pinion and configured to move through the first and second openings of the housing. The brake is attached to the housing. The pinion is rotatable in the first displacement position and the rack is movable in a direction toward the first displacement position relative to the second displacement position. The pinion engages the brake in the second displacement position and the brake inhibits rotation of the pinion which inhibits movement of the rack in a direction toward the second displacement position relative to the first displacement position.

In some configurations, the pinion further includes a gear, and the rack further comprises a plurality of teeth that mesh with the gear.

In some configurations, the pinion further includes flanges positioned on opposite sides of the gear, wherein the brake engages the flanges to inhibit rotation of the pinion.

In some configurations, the pinion has an axle that engages slots within the housing, and the axle moves laterally within the slots between the first and second displacement positions.

In some configurations, a directional lock includes a housing, a rack and pinion mechanism and a brake.

In some configurations, a directional lock includes a housing, at least one roller, a filament and at least one bearing surface. The housing defines an interior space, a first opening and a second opening. Each of the first and second openings communicates with the interior space. At least one roller is positioned within the interior space and rotatable relative to the housing. The at least one roller is configured to move between a first displacement position and a second displacement position. The filament is engaged with the at least one roller, the filament configured to move through the first and second openings of the housing. At least one bearing surface is positioned within the housing and configured to engage the at least one roller. The at least one roller is rotatable in the first position and the filament is movable in a direction toward the first displacement position relative to the second displacement position. The at least one roller engages the at least one bearing surface in the second position and the at least one bearing surface inhibits rotation of the at least one roller which inhibits movement of the filament in a direction toward the second displacement position relative to the first displacement position.

In some configurations, the at least one roller includes a pair of rollers, and the filament travels between the pair of rollers.

In some configurations, the at least one roller further comprising a tread positioned on an outer surface of the at least one roller being formed from at least one of an elastomeric, compressible or tactile material.

In some configurations, the pinion has an axle that engages slots within the housing, and the axle moves laterally within the slots between the first and second displacement positions.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 2 illustrates an exemplary headgear assembly coupled to a full face mask type interface.

FIG. 3 illustrates the exemplary headgear assembly in FIG. 2 coupled to a nasal mask.

FIG. 4 illustrates the exemplary headgear assembly in FIG. 2 coupled to a nasal pillows/prongs mask.

FIG. 6A is a side view of a directional lock and portion of a braided element of a circumference adjusting portion. The directional lock includes an arrangement that assists or initiates movement of a lock member of the directional lock. An outer housing of the directional lock is shown as transparent to show the underlying sleeve and lock member.

FIG. 6B is a side view of the directional lock of FIG. 6A in another position of the housing and sleeve.

FIG. 7 is a perspective view of the directional lock of FIG. 6A with the housing removed to illustrate the underlying components.

FIG. 8 is an enlarged view of a portion of the sleeve, lock member and catch arrangement of FIG. 7.

FIGS. 12A-12C include dashed lines to illustrate certain positions of the lock member and the sleeve.

FIG. 17 is a front view of the exemplary rack and pinion mechanism illustrating the positioning of the pinion relative to the housing during a retraction movement of the rack.

FIG. 18 is a cross-sectional front view of the exemplary rack and pinion mechanism in FIG. 17 illustrating the positioning of the pinion relative to the housing during a retraction movement of the rack.

FIG. 19 is a front view of the exemplary rack and pinion mechanism illustrating the positioning of the pinion relative to the housing during an extension movement of the rack.

FIG. 20 is a cross-sectional front view of the exemplary rack and pinion mechanism in FIG. 19 illustrating the positioning of the pinion relative to the housing during an extension movement of the rack.

FIG. 22A is a front-side view of the exemplary rack and pinion mechanism in FIG. 21.

FIG. 22B is a right-side view of the exemplary rack and pinion mechanism in FIG. 21.

FIG. 22C is a left-side view of the exemplary rack and pinion mechanism in FIG. 21.

FIG. 22D is a top-side view of the exemplary rack and pinion mechanism in FIG. 21.

FIG. 22E is a bottom-side view of the exemplary rack and pinion mechanism in FIG. 21.

FIG. 23A is an isometric view of the housing of the exemplary roller lock mechanism.

FIG. 23B is a cross-sectional front view of the housing of the exemplary roller lock mechanism.

FIG. 23C is a cross-sectional front view of the exemplary roller lock mechanism along a line 23C-23C in FIG. 22D.

FIG. 23D is a cross-sectional side view of the exemplary roller lock mechanism along a line 23D-23D in FIG. 22A.

FIG. 25A is a phantom view of the roller lock mechanism illustrating the positioning of the rollers relative to the housing in a retraction mode.

FIG. 25B is a phantom view of the roller lock mechanism illustrating the positioning of the rollers relative to the housing in an extension mode.

FIG. 25C is a phantom view of the roller lock mechanism illustrating the positioning of the rollers relative to bearing surfaces in the extension mode.

FIG. 26A is a front perspective view of a compact rack and pinion mechanism.

FIG. 26B is a top view of the compact rack and pinion mechanism.

FIG. 26C is a cross-sectional front view of the compact rack and pinion mechanism along a line 26C-26C in FIG. 26B.

FIG. 26D is a front view of the compact rack and pinion mechanism.

FIG. 27A is a front perspective view of a thick rack and pinion mechanism.

FIG. 27B is a top view of the thick rack and pinion mechanism.

FIG. 27C is a cross-sectional front view of the thick rack and pinion mechanism along a line 27C-27C in FIG. 27B.

FIG. 27D is a front view of the thick rack and pinion mechanism.

FIG. 28A is a front perspective view of a wide rack and pinion mechanism.

FIG. 28B is a top view of the wide rack and pinion mechanism.

FIG. 28C is a cross-sectional front view of the wide rack and pinion mechanism along a line 28C-28C in FIG. 28B.

FIG. 28D is a front view of the wide rack and pinion mechanism.

DETAILED DESCRIPTION

Figure 1:
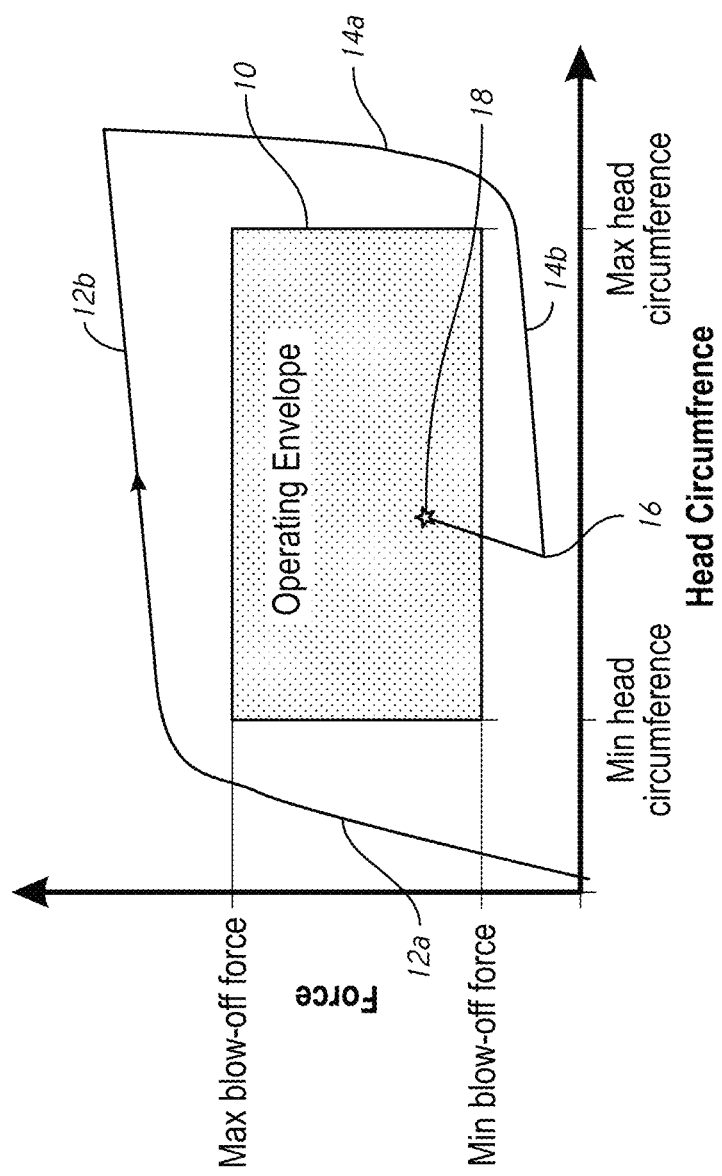
FIG. 1 is a graph of a force-deflection curve of an exemplary headgear arrangement.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Some embodiments disclosed herein involve a headgear system and/or an interface assembly incorporating a headgear system that upon fitment to the head of a user automatically adjusts to the correct size and, once in use, transforms in properties from an elasticated "stretchy" strap/strapping configuration to an "inelastic" strap/strapping configuration. In some configurations, the headgear (alone or as integrated in an interface assembly) exhibits a relatively small contraction force that tends to shorten the headgear. When coupled to a mask, the headgear and mask cooperate to define a perimeter of the interface assembly, which is reduced in length as a result of the contraction force toward or to a minimum perimeter length. Although not likely to be perfectly circular, the perimeter length is often referred to as a "circumference." Thus, with such an arrangement, the interface assembly can be positioned on the user's head and will automatically contract to or very near a proper head size, in a manner similar to an elasticated or "stretchy" headgear. The contraction force preferably is sufficient to support the weight of the interface assembly and at least substantially keep the interface assembly in place on the user's head at the smallest head size or minimum useful perimeter length of the interface assembly, which may or may not coincide with the minimum perimeter length. In some configurations, the retraction force can be sufficient to support the weight of a nasal cannula or other small interface, which can have a weight of about 50 grams, for example. In other configurations, the retraction force can be between about 0.5 Newtons and about 5.2 Newtons, or between about 1 Newton and about 2.6 Newtons, or between about 1 Newton and about 1.5 Newtons, including any value and sub-range within these ranges. In other configurations, the retraction force may be insufficient to support the weight of the interface and may require manual assistance to move the interface to a sealed position on the user's face. However, preferably, once the headgear is sufficiently retracted, it is then held in place by, for example, the directional lock(s). In some configurations, the contraction force is only sufficient or is configured to support the weight of the headgear.

However, in at least some configurations, the contraction force is less than is necessary to maintain the mask in sealed contact with the user's face during treatment/use. That is, the contraction force, alone, cannot resist the blow-off force. In some configurations, the contraction force is insufficient to resist the blow-off force throughout a range of usable perimeter lengths or headgear sizes. Therefore, the headgear and/or interface assembly also exhibits an inelastic behavior in response to forces tending to elongate the headgear or increase the perimeter length of the interface assembly. The headgear and/or interface assembly can have a locked mode that can produce a locking force tending to resist expansion, elongation or lengthening of the perimeter length. The locking force can be sufficient to resist elongation, or at least any significant elongation, of the perimeter length in response to blow-off forces. In some configurations, the locking force is sufficient to resist elongation in response to the highest blow-off forces expected with a variety of uses or treatments (e.g., Bi-Level or CPAP, NW, etc.). In some configurations, the locking force may be selected for one or more particular uses/therapies, but may not be suitable for all uses/therapies. In some configurations, the locking force may be selected to resist elongation in response to forces in addition to blow-off forces, such as hose pull forces, for example. Such additional forces can be referred to collectively herein as "hose pull forces" and such additional resistance to elongation can be referred to herein as a "reserve."

In some configurations, the headgear and/or interface assembly also exhibits a yield force, above which expansion or elongation of the perimeter length is permitted. Preferably, the yield force is greater than the expected blow-off force. In some configurations, the yield force is greater than the expected blow-off force and the hose pull force. Thus, such a headgear and/or interface assembly has a reserve. Preferably, the yield force is set low enough that a user can at least relatively conveniently apply an elongation force to the headgear and/or interface assembly sufficient to exceed the yield force in order to permit the interface assembly to lengthen and to be applied to the user's head. As described above, the contraction force reduces the perimeter length toward or to a proper head size.

In some configurations, the headgear and/or interface assembly automatically transitions between a contraction mode, a locked mode and a yield mode in response to the presence or absence of external forces. For example, the headgear and/or interface assembly moves toward or to the minimum perimeter length in the absence of external lengthening or expanding forces. A lengthening or expansion force that is greater than the yield force can be applied to increase the perimeter length of the headgear and/or interface assembly to a length sufficient to permit the interface assembly to be positioned on the user's head. Once the lengthening or expansion force is removed (or reduced to below the contraction force), the contraction force acts to automatically reduce the perimeter length to or substantially to the proper head size such that the interface assembly is supported on the user's head. Upon the start of treatment (application of blow-off force) and/or application of hose pull force, the headgear and/or interface assembly automatically transforms to the locked mode to resist elongation, or at least resist any significant elongation, or increase of the perimeter length. At the end of treatment, or at any time as desired, a force above the yield force can be applied to the headgear and/or interface assembly to increase the perimeter length and permit removal of the interface assembly from the user's head.

Advantageously, with such an arrangement, micro-adjustments of the perimeter length of the headgear and/or interface assembly can be accomplished quickly and conveniently. For example, during treatment or use, the mask can be manipulated to effect micro-adjustment of the perimeter length. For instance, in the event of a leak between the mask and the user's face, the mask can be wiggled or otherwise moved to effect a micro-adjustment of the perimeter length to address the leak. In some cases, the seal of the mask may be compressed against the user's face, which can allow the contraction force to automatically reduce the perimeter length. Upon release of the mask, the headgear and/or interface assembly locks at, or very near, the reduced perimeter length. Thus, such configurations permit the headgear and/or interface assembly to micro-adjust, or move to an adjusted perimeter length, as a result of small manipulations (e.g., wiggling) of the mask. Manipulation of other portions of the interface assembly (e.g., headgear or breathing tube/gases conduit) can similarly result in micro-adjustment. Because of the nature of the human head and/or the conditions under which interface assemblies are used, quick and convenient micro-adjustment can dramatically improve performance and user satisfaction of an interface assembly. Treatment often occurs at night and/or under other situations when the user is lying down. Thus, the headgear can be in contact with surface, such as a pillow or bed. Movement of the user's head relative to such surfaces can cause movement of the headgear, which can alter the fit of the headgear. For example, hair can move or "compress" beneath the headgear, which can alter the fit. The headgear straps may move up, down or rotationally on the head, which can alter the fit. Such alterations in fit can result in leaks between the mask and the user's face. The above-described adjustment technology can permit such changes in fit to be addressed automatically or with small manipulations of the mask or other portions of the interface assembly. Moreover, the interface assembly can be removed and reapplied and automatically adjust to at or very near a proper headgear size. In contrast, if conventional non-stretch headgear is moved from its desired adjustment position, such as by mistake or as a result of cleaning, it can be difficult and time-consuming to reestablish the desired adjustment position. Conventional elasticated headgear addresses the adjustment issue, but because the contraction force must resist the highest expected blow-off and hose pull forces at the smallest useable headgear size, elasticated headgear applies a relatively large pressure to the user's head that is only partially relieved by the application of blow-off force. Such pressure may be substantial for a user with a relatively large head size and low treatment pressure.

In some configurations, some amount of movement may occur in the headgear and/or interface assembly during transition from the elastic mode to the locked mode. For example, with some directional lock arrangements, the perimeter length may increase slightly during the transition from elastic mode to locked mode. In some cases, there exists a compromise between increased yield force and reduced perimeter length change during transition. Thus, references to any particular positions of the headgear and/or interface assembly or perimeter lengths can include such slight length changes during transition, if present.

The following example of the above-described adjustment technology is based on the delivery of CPAP. The series of graphs describe a typical operating envelope that a headgear system must be designed to operate over and how various current embodiments operate relative to that envelope. The envelope may comprise an entire CPAP treatment universe, that is, an entire range of typical, probable or possible CPAP pressures and an entire range of typical, probable or possible head sizes. Or, the envelope may comprise a subset of the CPAP treatment universe, such as a subset of pressures (e.g., low pressure or high pressure CPAP) or head (headgear or interface assembly) sizes (e.g., small, medium or large). The principles discussed in connection with CPAP treatment may apply to other treatments, as well.

FIG. 1 illustrates a graph of a force-deflection curve of an example of a headgear arrangement or interface assembly comprising a headgear arrangement. The head circumference axis of the graph may represent the head circumference of a user or the circumference or perimeter length of the headgear arrangement or interface assembly that fits or is intended to fit a user.

The graph of FIG. 1 also illustrates an operating envelope 10 relevant to the headgear arrangement or interface assembly. The operating envelope 10 is illustrated as a rectangular area defined between minimum and maximum blow-off forces or forces applied to the headgear arrangement or interface assembly as a result of the therapy and minimum and maximum head sizes or circumferences/perimeter lengths of the headgear arrangement. The operating envelope 10 can be specific to a therapy (e.g., CPAP or bi-level PAP) or can cover multiple therapies. Similarly, the head size or circumference/perimeter length can be specific to a size of headgear arrangement or can cover multiple sizes. The operating envelope 10 can be used to establish functional or behavioral criteria of a particular headgear arrangement and is utilized herein to illustrate features or behaviors of certain disclosed embodiments.

A graph containing an example force-deflection curve of an example headgear arrangement or interface assembly (referred to as "headgear" for convenience in the discussion of the graph) is illustrated relative to the example operating envelope 10. The curve originates at or near the origin of the graph, which may represent approximately zero force and a minimum circumference or perimeter length (referred to as "circumference" for convenience in the discussion of the graph) of the headgear. The minimum circumference is greater than zero, but typically at a value below a minimum head circumference (taking into consideration the interface, if any) of the intended user or range of users.

To place the headgear onto the user, typically, the headgear will be elongated to a circumference greater than the actual head circumference of the user. Typically, a rear portion of the headgear will be placed on the rear of the user's head and the user will grasp the front of the headgear (e.g., the mask or other interface) and apply a pulling force to elongate the headgear and move the mask or other interface over the crown of the head and toward the face.

As illustrated in the graph of FIG. 1, the example force-deflection curve initially rises with a steep pitch, in which the force increases a substantial amount with a relatively small increase in the circumference. In some configurations, the force-deflection curve rises above the maximum force level of the operating envelope 10 before reaching the minimum circumference of the operating envelope 10. This portion of the curve can be referred to as an initial elongation portion 12a.

At some location above the maximum force of the operating envelope 10, the force-deflection curve transitions to a shallower pitch, in which the circumference increases a substantial amount with a relatively small increase in the force. This shallow pitch portion of the force-deflection curve can relate to a yield force of the retention arrangement of the headgear. Preferably, the shallow pitch portion, which can be referred to as an elongation portion 12b, of the force-deflection curve extends at or above the maximum force level of the operating envelope 10 along a portion or an entirety of the circumference range of the operating envelope 10. In some configurations, the elongation portion 12b extends beyond the maximum circumference level of the operating envelope 10. That is, the headgear can be configured to achieve a greater circumference than the intended maximum head circumference to allow the headgear to be conveniently placed onto a user having the maximum head circumference of the operating envelope 10 of the headgear. In use, especially with users having head sizes on the smaller end of the operating envelope 10, the headgear may not be elongated to a maximum circumference during donning and, in some cases, may not be elongated beyond the maximum circumference level of the operating envelope 10.

After the headgear has been elongated to the maximum circumference, to a circumference greater than the operating envelope 10 or, in use, to some other circumference sufficient to allow donning onto the user, the illustrated force-deflection curve drops steeply (initial retraction portion 14a) and then transitions to a relatively shallow portion, in which the circumference reduces substantially with a relatively small change in force. This shallow portion of the curve can be referred to as a retraction portion 14b. Preferably, in the retraction portion 14b, the headgear reduces in circumference at a relatively low force level until the headgear reaches or is substantially close to an appropriate circumference to fit the user's head. The headgear can be positioned on the user's head at this low force level (the left end of the retraction portion 14b or "fit point 16") until therapy is initiated or until another force attempting to elongate the headgear is applied.

Advantageously, this relatively low force level allows the headgear to be comfortable for the user. In some configurations, the retraction portion 14b of the force-deflection curve is at or below the minimum force level of the operating envelope 10. Thus, in such an arrangement, the retraction force of the headgear can be lower than that necessary or desirable to resist minimum forces induced in the headgear by the therapy (e.g., a low CPAP level). Accordingly, even at low therapy levels, the headgear can be configured to produce only enough retention force to resist the therapy-induced forces because the minimum force level of the operating envelope 10 is above the retraction portion 14b of the force-deflection curve. In some configurations, as described below, the retraction portion 14b of the force deflection curve could fall within the operating envelope 10. Such an arrangement can be referred to as exhibiting "composite" behavior. However, preferably, the retraction portion 14b of a composite-behavior headgear force-deflection curve remains below the maximum force level of the operating envelope 10.

When therapy is commenced, or another elongating force is applied to the headgear, the force deflection curve rises relatively steeply from the fit point 16 to a point within the operating envelope 10 at which the retention force of the headgear balances with the force induced by the therapy and/or other forces (e.g., hose pull forces) attempting to elongate the headgear. Such a point can be referred to as a balanced fit point 18. The force-deflection curve between the fit point 16 and the balanced fit point 18 can have substantially the same slope as the initial elongation portion 12a. The actual location of the balanced fit point 18 can be anywhere within the operating envelope 10 depending on the actual force induced by the therapy and the actual head size of the user. In any particular case, the force in the headgear, which is applied over an area related to headgear size as a pressure to the user, is substantially only the force necessary to counteract the forces induced by the therapy. Thus, in at least some configurations, the pressure applied to the user can be minimized for any particular headgear size and shape for the particular level of therapy utilized. The elongation portion 12b of the force-deflection curve can be spaced above the maximum force level of the operating envelope 10 to provide a reserve in which additional forces (e.g., hose pull forces) can be applied without elongation of the headgear. Once sufficient force is applied to the headgear to reach the elongation portion 12b of the force-deflection curve, elongation of the headgear can occur. However, the headgear can be designed or configured to have a force-deflection curve that accommodates expected or usual therapy forces and hose pull forces or any combination thereof.

As described above, in at least some configurations, the user can manipulate the headgear to cause a micro-adjustment of the perimeter length. Advantageously, such an arrangement allows the user to, for example, address leaks or tighten or loosen the headgear (reduce the perimeter length) to a desired level by simply grasping the mask or other interface and moving (e.g., wiggling) the mask or other interface relative to the user's face and a rear portion of the headgear. The mask or other interface can be moved or adjusted in a plurality of directions, including toward and away from the user's face or in a rotational manner (e.g., about a vertical or horizontal/lateral axis). Movement toward the face can result in a reduction of the perimeter length or tightening of the headgear to, for example, achieve a fit that is toward the tight end of the spectrum of an acceptable or desirable fit, which can be referred to as a "tight fit." Movement away from the face can result in elongation of the perimeter length or loosening of the headgear to, for example, achieve a fit that is toward the loose end of the spectrum of an acceptable or desirable fit, which can be referred to as a "loose fit." Rotational movement about a vertical axis can cause one side of the headgear to tighten and the other side to remain the same or loosen. Rotation about a horizontal or lateral axis can cause one of an upper or lower portion of the headgear to tighten and the other of the upper or lower portion to loosen.

As described above, it is not necessary in all configurations that the retraction portion 14b of the force-deflection curve be located below a minimum force level of the operating envelope 10. The headgear can be designed or configured to position the retraction portion 14b of the force-deflection curve within the operating envelope 10 and at a level that provides a sufficient degree of comfort to the user. In some cases, the user may desire that the headgear apply some degree of force in order to provide the user with some tactile feedback that provides a feeling of comfort that the headgear is securely holding the interface in place. Such force applied by the headgear may, for some users, fall within the operating envelope 10 of the particular therapy. Thus, with such an arrangement, under at least some conditions, the retraction force of the headgear may be sufficient to resist therapy forces at least as some lower therapy levels and/or certain larger head sizes.

FIGS. 2-4 illustrate an example headgear assembly 1600 that, in at least some configurations, can be utilized with two or more interface types. For example, FIG. 2 illustrates the headgear assembly 1600 as forming a modular component of an interface assembly comprising a full face mask type interface 1650. The headgear assembly 1600 can comprise a portion 1602 that engages the interface 1650 or can otherwise be coupled to the interface 1650. In some configurations, the engagement or coupling portion 1602 of the headgear assembly 1600 can be engaged or coupled with at least one other type of interface. For example, FIG. 3 illustrates the headgear assembly 1600 of FIG. 2 (shown in dashed line) supporting a nasal mask 1660 and FIG. 4 illustrates the headgear assembly 1600 of FIG. 2 (shown in dashed line) supporting a nasal pillows/prongs mask 1670. Thus, with such a modular arrangement, a single headgear assembly can be utilized with multiple types of interfaces. Advantageously, the on-demand resistance feature of the headgear assembly as described herein allows the single headgear assembly to operate in a suitable manner with the different interface types. For example, the retention force provided by the headgear can automatically adjust to the force applied to the headgear by the particular interface that is used. However, in other arrangements, the headgear assembly 1600 can be specific to an interface type.

The headgear assembly 1600 can be generally similar to the other headgear assemblies disclosed in Applicant's Application No. PCT/NZ2014/000074 (Publication No. WO2014/175752), the entirety of which is incorporated by reference herein. In particular, the illustrated headgear assembly 1600 includes a headgear rear portion 1604, the interface coupling portion 1602 and a length or circumference adjusting portion 1606 that is interposed between the headgear rear portion 1604 and the interface coupling portion 1602. The headgear rear portion 1604 is configured in use to contact a rear portion of the user's head. The interface coupling portion 1602 is configured in use to be coupled to an interface such that the headgear assembly 1600 can support the interface in an appropriate position on the face of the user. The length or circumference adjusting portion 1606 is configured in use to permit a position of the interface coupling portion 1602 to be adjusted relative to the headgear rear portion 1604 such that the headgear assembly 1600 can be adjusted to the head size of a particular user. Thus, the length or circumference adjusting portion 1606 can permit a perimeter length or circumference of the headgear to be adjusted to allow the headgear assembly 1600 to fit the head size of a particular user.

The headgear rear portion 1604 can be of any suitable arrangement, such as the same as or similar to any of those described herein or in Applicant's Application No. PCT/NZ2014/000074. Preferably, the headgear rear portion 1604 engages the user's head and provides a relatively stable platform for connection of the interface, such as utilizing the interface coupling portion 1602 and the circumference adjusting portion 1606. Thus, in at least some configurations, the headgear rear portion 1604 is substantially inelastic such that it holds its shape and effective length in response to applied forces within a range that is typical or expected for the intended application. The headgear rear portion 1604 can include a top strap portion 1608 that extends over the top of the user's head and a rear strap portion 1610 that extends around the back of the user's head. The top strap portion 1608 and rear strap portion 1610 can be separate or coupled in any suitable manner, such as by an intermediate connecting portion 1612.

The length or circumference adjusting portion 1606 can be of any suitable arrangement, such as the same as or similar to any of those described herein or in Applicant's Application No. PCT/NZ2014/000074. The circumference adjusting portion 1606 can comprise two pair of adjustment elements 1614 in which one pair of adjustment elements 1614 are positioned on each side of the headgear assembly 1600. Thus, the illustrated headgear arrangement 1600 can be generally described or categorized as a two retention plane headgear type. The headgear arrangement 1600 can be described as a two retention plane, forward converge headgear type or possibly a hybrid of a two retention plane, forward converge headgear type and a two retention plane, separated/angled headgear type.

Each pair of the adjustment elements 1614 can couple one side of the headgear rear portion 1604 with one side of the interface coupling portion 1602. The pair of adjustment elements 1614 one each side are coupled to the headgear rear portion 1604 at spaced locations. For example, one of the adjustment elements 1614 is coupled to the headgear rear portion 1604 at or near a portion of the top strap 1608 and the other of the adjustment elements 1614 is coupled the headgear rear portion 1604 at or near a portion of the rear strap 1610. In the illustrated arrangement, the upper adjustment elements 1614 are coupled to forward extensions of the headgear rear portion 1604 that extend in a forward direction from a portion of the top strap 1608 at or near a location above the user's ear. The lower adjustment elements 1614 are coupled to ends of the rear strap 1610 of the headgear rear portion 1604.

The adjustment elements 1614 are adjustable in length between a retracted length and an extended length. In some configurations, the adjustment elements 1614 cooperate to provide all or substantially all of the adjustment of a circumference of the headgear assembly 1600. Each of the adjustment elements 1614 can also include an elastic element or biasing arrangement that biases the adjustment element 1614 toward one of the retracted or extended lengths. Preferably, the adjustment elements 1614 are biased toward a retracted length, such that the headgear assembly 1600 is biased toward its smallest circumference. Such an arrangement permits the headgear assembly 1600 to be extended and then automatically retract to fit the particular user under the biasing force of the elastic element or other biasing arrangement of the adjustment element(s) 1614. In addition, preferably, the adjustment elements 1614 define a hard stop at a maximum extended length to limit extension of the headgear 1600 and define a maximum circumference of the headgear 1600.

In some configurations, each of the adjustment elements 1614 comprises a braided element, which can extend or retract in length. The braided element can comprise one or more elastic elements in parallel with the braided element. The elastic elements can be separate from the braided element or incorporated in the braided element. In some configurations, the elastic elements are contained in internal spaces between filaments of the braided element. An example of suitable braided elements is described in connection with FIGS. 46-54 of Applicant's patent application no. PCT/NZ2014/000074. However, other suitable constructions or arrangements can also be used. Alternatively, elastic element(s) or biasing element(s) can be located within the interface coupling portion and can interact with the core members to pull the core members into the interface coupling portion.

The interface coupling portion 1602 of the headgear assembly 1600 can extend between the pair of adjustment elements 1614 that comprise the circumference adjusting portion 1606. In some configurations, the interface coupling portion 1602 can be relatively rigid. In some configurations, the interface coupling portion 1602 is coupled directly to the adjustment elements 1614. As described above, the interface coupling portion 1602 can facilitate connection of the headgear assembly 1600 to an interface. However, the interface coupling portion 1602 can also accommodate at least a portion of one or more directional locks 1616. In the illustrated arrangement, two pair of directional locks 1616 is provided, with one directional lock 1616 associated with each one of the adjustment elements 1614. Portions (e.g., housings 1810) of the directional locks 1616 can be located at each end of the interface coupling portion 1602. In some configurations, a core member 1830 associated with each of the directional locks 1616 is coupled to the headgear rear portion 1604, extends along or through the adjustment element 1614, through the housing 1810 of the directional lock 1616 and into a collection space 1622. The collection space 1622 can be defined by a collection tube or conduit, which can be a separate member from or can be incorporated into the interface coupling portion 1602. The housing 1810 of the directional lock 1616 can comprise one or more members or elements (e.g., lock washers or lock jaws) that interact with the core member 1830 to selectively allow retraction of the headgear assembly 1600 or lock the headgear assembly 1600 in a particular circumference and inhibit or prevent extension of the headgear at least at forces below the yield force provided by of the directional lock(s). Additional particulars of the operation of the directional locks 1616 are described herein and in Applicant's patent application no. PCT/NZ2014/000074.

In the illustrated arrangement, the directional locks 1616 on each side of the interface coupling portion 1602 are vertically stacked or positioned side-by-side. Although the directional locks 1616 are illustrated as separate units, in some configurations portions of the directional locks 1616 can be integrated. For example, a single housing could contain individual lock elements that interact with the separate core members of each adjustment element.

The interface coupling portion 1602 can be curved and the collection spaces 1622 (e.g., defined by collection tubes or channels) can be curved along with the interface coupling portion 1602. In the illustrated arrangement, a center portion of the interface coupling portion 1602 is located above end portions of the interface coupling portion 1602. Furthermore, when viewed from the front, side portions of interface coupling portion 1602 curve downwardly from the center portion. Thus, the interface coupling portion 1602 can complement or correspond to the shape of a body or shell portion of the full face mask interface 1650. The center portion of the interface coupling portion 1602 can be located above an elbow or other conduit connector of the mask 1650. Similarly, the interface coupling portion 1602 can be configured to complement or correspond to the shape of a body or shell portion of the nasal mask interface 1660. The center portion of the interface coupling portion 1602 can be located above an elbow or other conduit connector of the nasal mask 1660. The interface coupling portion 1602 can be configured to complement or correspond to the shape of a body of the nasal pillows/prongs mask 1670. The center portion of the interface coupling portion 1602 can be located above an elbow or other conduit connector of the nasal pillows/prongs mask 1670. In some configurations, the interface coupling portion 1602 can be located between the elbow or other conduit connector and the pillows/prongs of the nasal pillows/prongs mask 1670.

FIGS. 5A to 5D show an embodiment of a directional lock 1616 comprising a housing 1810, a first and a second lock element (e.g., washer 1820, 1822, respectively), and a core member 1830. The housing comprises a first and a second chamber 1840, 1842 wherein the first and second chambers 1840, 1842 are configured to house the first and second lock washers 1820, 1822, respectively. In the illustrated arrangement, the first and second chambers 1840, 1842 are separated by an internal wall 1812 of the housing 1810. However, in other arrangements, the first and second chambers 1840, 1842 are not necessarily physically separate spaces, but can be portions of a chamber. The housing 1810 has two end walls 1814, which along with the internal wall 1812, have an elongate core opening 1860 through which the core member 1830 passes. The core openings 1860 are substantially aligned with each other. The core opening 1860 of the end wall 1814 shown on the right side of the figures is larger than the core opening of the internal wall 1812 and the end wall 1814 shown on the left of the figures. This allows for manipulation of the path of the core member 1830 through the housing 1810. The first and second chambers 1840, 1842 are each delimited by the internal wall 1812, one of the end walls 1814 and a pair of side walls 1816; wherein the side walls 1816 extend between the end walls 1814 of the housing 1810. The first and second chambers 1840, 1842 can be configured to be open at one or both of a top and a bottom of the housing 1810 to allow for insertion of the lock washers 1820, 1822.

Each of the first and second chambers 1840, 1842 has a pair of washer retainers 1850 that are aligned on opposing side walls 1816 of the housing 1810. Each pair of washer retainers 1850 is configured to pivotally retain one of the first or second lock washers 1820, 1822 within the respective first or second chamber 1840, 1842. The washer retainers comprise a circular bush 1852 and an elongate slot 1854, wherein circular bushes 1852 intersect with the bottom of the housing such that an entrance is formed. The entrance is configured to allow the first and/or second lock washers 1820, 1822 to be received into the washer retainers 1850. The slot 1854 extends radially from the circular bush 1852 towards the top of the housing 1810 and facilitate flexing of the housing 1810 to allow insertion of the lock washers 1820, 1822 into the bushes 1852.

The first and second washers 1820, 1822 comprise a cylindrical shaft 1824 and an arm 1826 that extends from the shaft 1824. The cylindrical shaft 1824 is substantially the same width W as the housing 1810 and the arm 1826 is narrower to fit within the first and second chambers 1840, 1842. In the illustrated arrangement, the arm 1826 comprises a first section 1872 and a second section 1874, wherein the first section 1872 extends radially or perpendicularly from the cylindrical shaft 1824 and the second section 1874 extends at an angle from the end of the first section 1872. The first section 1872 of the arm 1826 of the first washer 1820 is shorter than the first section 1872 of the arm 1826 of the second washer 1822. The angle between the first and second sections 1872, 1874 of the arm 1826 of the first washer 1820 is greater than the corresponding angle of the second washer 1822. The angles can be selected such that the second section 1874 of one or both of the first and second washers 1820, 1822 lies substantially flat against the corresponding wall (e.g., internal wall 1812 and end wall 1814, respectively) of the housing 1810 in one position of the washers 1820, 1822. The second section 1874 of the arm 1826 comprises a centrally located circular aperture 1876 configured to receive the core member 1830. The first and second chambers 1840, 1842 differ in size according to the size of the washer that is to be housed within it, i.e. the first chamber 1840 is smaller than the second chamber 1842 because the first washer 1820 is smaller than the second washer 1822.

The cylindrical shafts 1824 of the first and second lock washers 1820, 1822 have a diameter substantially the same as that of the circular bushes 1852 of the washer retainer 1850, and are configured to be received and retained by the circular bush 1852 in a snap-fit configuration. The snap-fit configuration is provided by the entrance of the circular bush 1852 being narrower than the diameter of the cylindrical shaft 1824. As described above, the slots 1854 of the washer retainers 1850 are configured to allow the entrance to be flexed open to increase the ease with which the first and second lock washers 1820, 1822 can be pushed through the entrances and assembled to the housing 1810. Once assembled within the first and second chambers 1840, 1842 of the housing 1810, the first and second washers 1820, 1822 can pivot back and forward around a central axis that runs through the cylindrical shaft 1824.

Figure 5A:
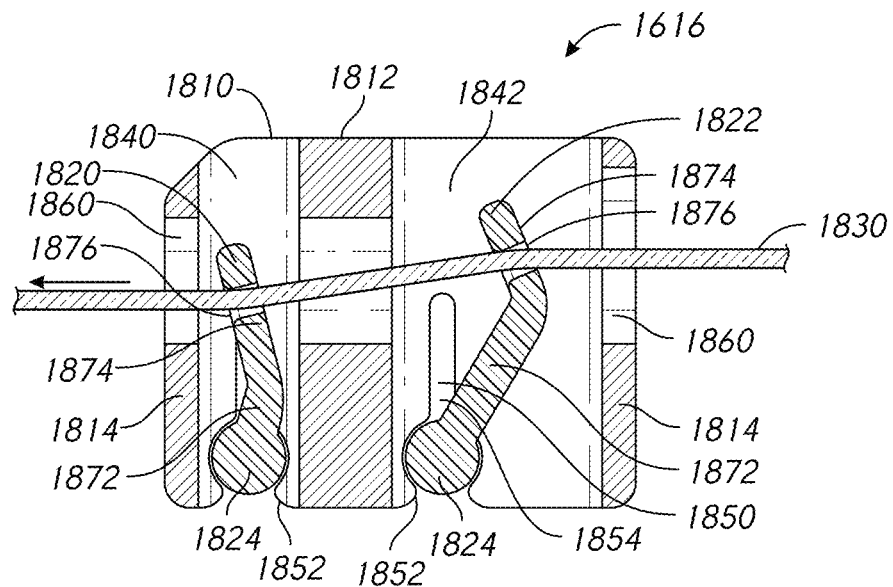
FIG. 5A is a cross-sectional view of a directional lock in a locked position.
Figure 5B:
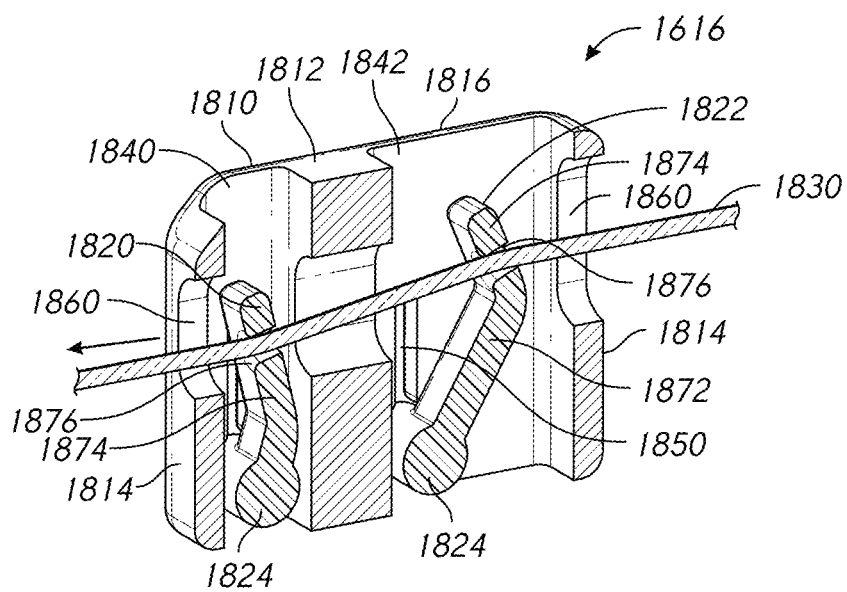
FIG. 5B is a perspective cross-sectional view of the directional lock in FIG. 5A in the locked position.

The core member 1830 is configured to pass through the core openings 1860 of the housing 1810 and the apertures 1876 of the first and second washers 1820, 1822. Application of a tension force to the core member 1830 causes the first and second lock washers 1820, 1822 to pivot back and/or forward between a locked position and/or open position. FIGS. 5A and 5B show the directional lock in a locked configuration in which a force is applied to the core member 1830 in a direction towards the left side of the figure (as indicated by the arrow). The force applied to the core member 1830 in this configuration causes the first and second lock washers 1820, 1822 to pivot in an anti-clockwise direction, such that the path of the core member 1830 through the directional lock 1616 is non-linear or tortuous and movement of the core member 1830 is restricted. Thus, relative movement between the core member 1830 and the housing 1810 is restricted. With such an arrangement, the extension of the circumference adjusting portion 1606 can be restricted or prevented within the operating range of the directional lock 1616.

Figure 5C:
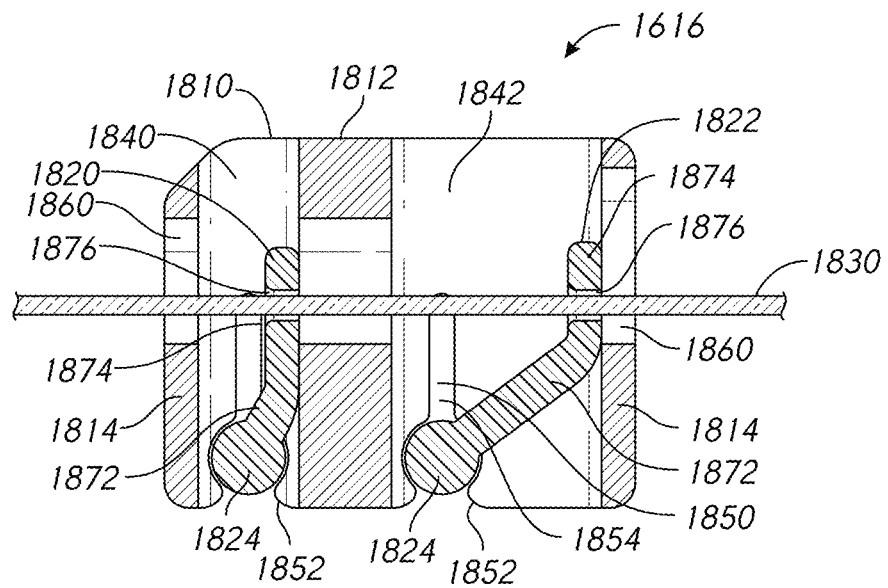
FIG. 5C is a cross-sectional view of the directional lock in FIG. 5A in the unlocked position.
Figure 5D:
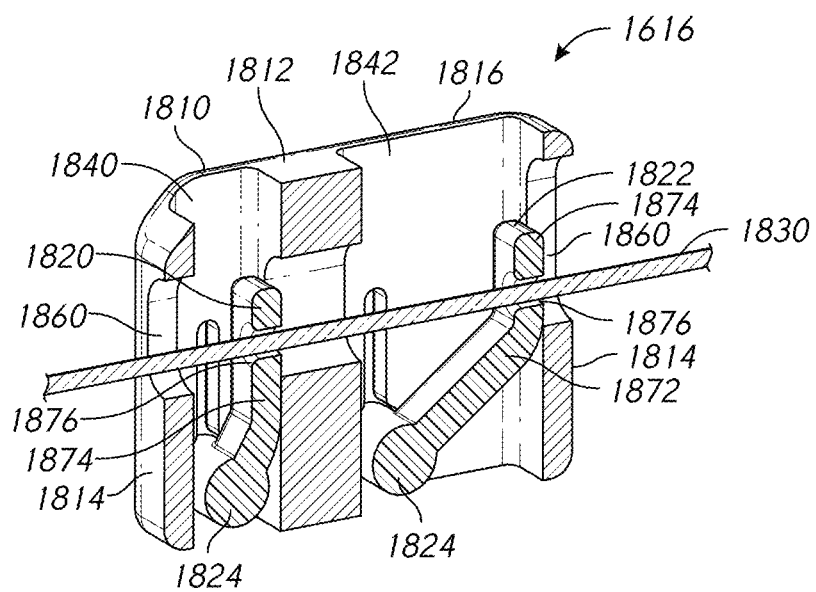
FIG. 5D is a perspective cross-sectional view of the directional lock in FIG. 5A in the unlocked position.

FIGS. 5C and 5D show the directional lock in an open configuration in which a force is applied to the core member 1830 in a direction towards the right side of the figure (as indicated by the arrow). In this configuration, the first and second lock washers 1820, 1822 are pivoted in a clockwise direction such that the circular apertures 1876 and core openings 1860 are aligned in a substantially straight line. This provides a smooth path for the core member 1830 to be pulled substantially freely through the directional lock 1616. Thus, relative movement between the core member 1830 and the housing 1810 is permitted. With such an arrangement, retraction of the circumference adjusting portion 1606 can be permitted with a relatively small retraction force. Additional particulars of the operation of the directional locks 1616 are described herein and in Applicant's patent application no. PCT/NZ2014/000074.

FIGS. 6A-13 illustrate a modification of the directional lock 1616 of FIGS. 2-5D, which can be incorporated in a headgear or headgear and interface, such as the headgear 1600 and any of the interfaces 1650, 1660, 1670 of FIGS. 2-4. Thus, portions of the directional lock 1616, headgear or interface not specifically described in connection with FIGS. 6A-13 can be the same as or similar to corresponding structure of FIGS. 2-5, or can be of another suitable arrangement. The same reference numbers are used to refer to the same or corresponding components or features between the directional lock 1616 of FIGS. 2-5D and the directional lock 1616 of FIGS. 6A-13.

The directional lock 1616 of FIGS. 6A-13 includes a single lock element, such as a lock washer 1822. However, in other arrangements, the directional lock 1616 could include two, or possibly more, lock elements similar to the directional lock 1616 of FIGS. 2-5D. The lock washer 1822 is configured to move between a released position, in which the core member 1830 can move through the aperture 1876 with less resistance, and a locked position, in which the core member 1830 can move through the aperture 1876 with greater resistance. As described above, when in the locked position, preferably movement of the core member 1830 relative to the lock washer 1822 is inhibited in response to normal or expected blow-off forces. In some configurations, relative movement between the core member 1830 and the lock washer 1822 is inhibited in response to forces above the normal or expected blow-off forces so that the directional lock 1616 can accommodate hose pull or other extraneous forces. However, movement of the core member 1830 relative to the lock washer 1822 preferably is permitted in response to a force applied by the user to deliberately extend the circumference adjusting portion 1606. The resistance offered by the directional lock 1616 can be tuned to the particular application and in view of the number of directional locks 1616 utilized in the interface assembly.

In at least one embodiment, the directional lock 1616 may include a lock activator to ensure activation of the lock element. The lock activator is configured to activate, promote, or assist the lock element, such as, in particular, during initial displacement or elongation of the headgear. In some embodiments, the lock activator is configured to activate prior to any elongation of the headgear. In other words, the lock activator initiates or activates at a lower force than the biasing element of the headgear. This may be particularly beneficial, because the lock activator may reduce the manufacturing tolerances associated with the directional lock components and/or core. The directional lock 1616 of FIGS. 6A-13 comprises one example of an arrangement configured to assist in the activation of the lock washer 1822 or movement of the lock washer 1822 in a locking direction from a position relatively closer to the released position towards a position relatively closer to the locked position. In the illustrated arrangement, the directional lock 1616 includes a catch arrangement 1900 configured to contact the lock washer 1822 and move the lock washer 1822 in the locking direction. The illustrated catch arrangement 1900 comprises a catch arm 1902 and a catch end 1904. The catch end 1904 is configured to contact the lock washer 1822 to move the lock washer 1822 in the locking direction. In the illustrated arrangement, the catch arm 1902 extends through a vertically-extending catch aperture 1906 in the lock washer 1822. However, other arrangements are also possible, such as the catch arm 1902 extending beside the lock washer 1822, for example.

In the illustrated arrangement, the lock washer 1822 is coupled to or carried by a first component and the catch arrangement 1900 is coupled to or carried by a second component that is movable relative to the first component. Relative movement of the first component and the second component can cause the catch arrangement 1900 to move the lock washer 1822 in the locking direction. In the illustrated arrangement, the first component is a housing 1810, which can be similar to the housing 1810 of FIGS. 2-5D, and the second component is a sleeve 1910. In the illustrated arrangement, the sleeve 1910 is coupled to the circumference adjusting portion 1606 by any suitable arrangement. In some configurations, the sleeve 1910 can be overmolded onto the braided element 1880 of the circumference adjusting portion 1606. As described above, the housing 1810 can be coupled to the coupling portion 1602 or directly to the interface 1650, 1660, 1670.

The illustrated sleeve 1910 defines a conduit portion 1912 and a cuff portion 1914. The cuff 1914 can surround and/or couple the sleeve 1910 to the braided element 1880 of the circumference adjusting portion 1606. A passage or sleeve interior space 1916 extends longitudinally through the sleeve 1910. The sleeve passage 1916 has a first opening and a second opening at opposing ends of the sleeve 1910. The core member 1830 passes through the sleeve passage 1916. The housing 1810 defines an interior passage or space 1860 that has an opening on each end of the housing 1810 and is configured to receive the sleeve 1910. In the illustrated arrangement, the conduit portion 1912 is received within the interior passage 1860 of the housing 1810.

Figure 9:
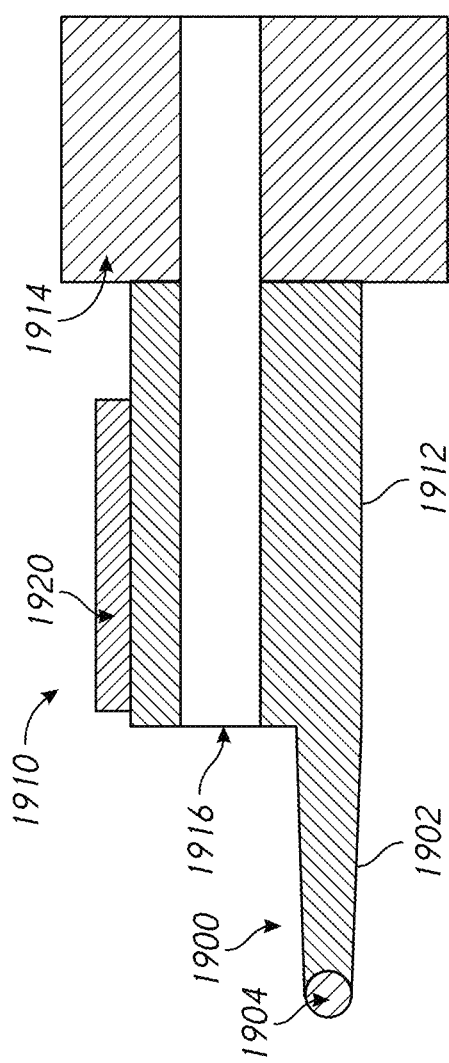
FIG. 9 is a longitudinal sectional view of the sleeve.
Figure 10:
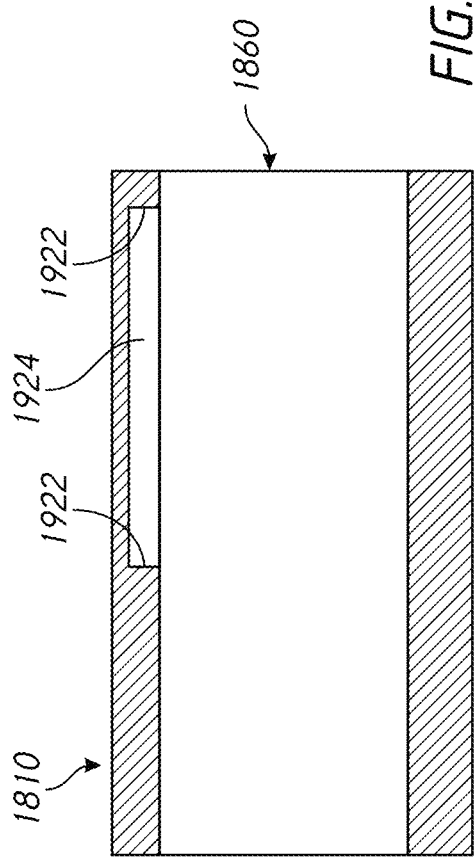
FIG. 10 is a longitudinal sectional view of the housing.

As described above, the sleeve 1910 is movable relative to the housing 1810. In the illustrated arrangement, the movement between the sleeve 1910 and the housing 1810 is limited. For example, the conduit portion 1912 of the sleeve 1910 includes one or more stop guides 1920. In some configurations, the stop guide 1920 is an elongate protrusion that extends lengthwise along the conduit portion 1912. The stop guide or guides 1920 can be positioned in any suitable location on the conduit portion 1912. In FIG. 7, stop guides 1920 are located on each side of the sleeve 1910. In FIG. 8, stop guides 1920 are located on the top and bottom of the sleeve 1910. In FIG. 9, a stop guide 1920 is located on the top of the sleeve 1910. A stop guide 1920 can be located at any one or any combination of these locations, or at other suitable locations. As illustrated in FIG. 10, the housing 1810 comprises stops 1922 configured to contact the stop guide 1920 to limit relative movement of the housing 1810 and the sleeve 1910. In the illustrated arrangement, the stops 1922 are defined by ends of a displacement slot 1924. However, the stops 1922 can be defined by any suitable structure.

With reference to FIGS. 6A and 6B, the directional lock 1616 is illustrated in a released position (FIG. 6A) and moved toward a locked position (FIG. 6B). The positions of FIGS. 6A and 6B are the respective terminal positions between the housing 1810 and the sleeve 1910 as defined by the stops 1922. In FIGS. 6A and 6B, the housing 1810 is shown in one position and the sleeve 1910 is shown in two positions relative to the housing 1810. As illustrated, as the sleeve 1910 moves relative to the housing 1810, the catch end 1904 contacts the lock washer 1822, if necessary, to ensure the lock washer 1822 is activated or moved in the locking direction.

Figure 11A:
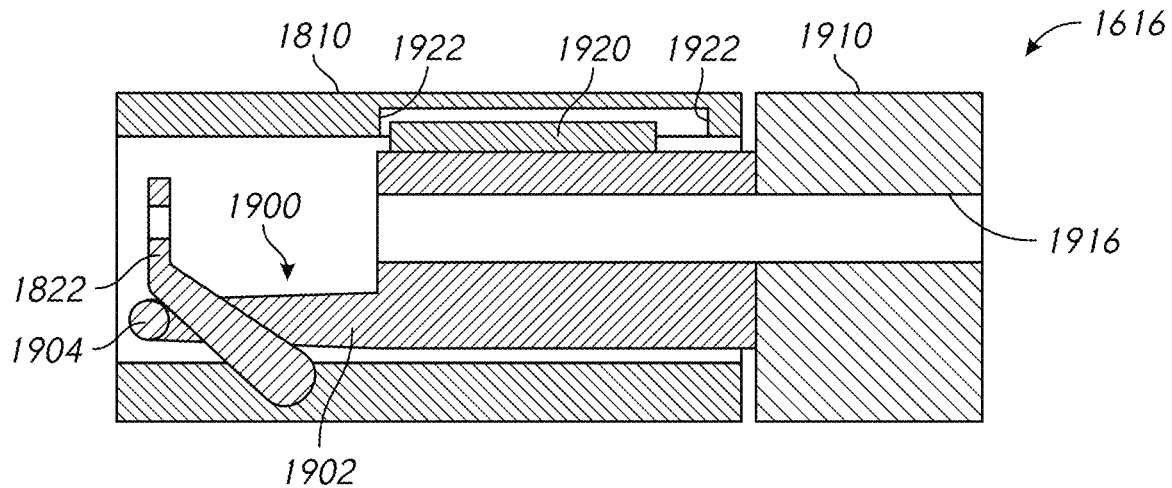
FIG. 11A is a longitudinal sectional view of the directional lock of FIG. 6A in a released position.
Figure 11B:
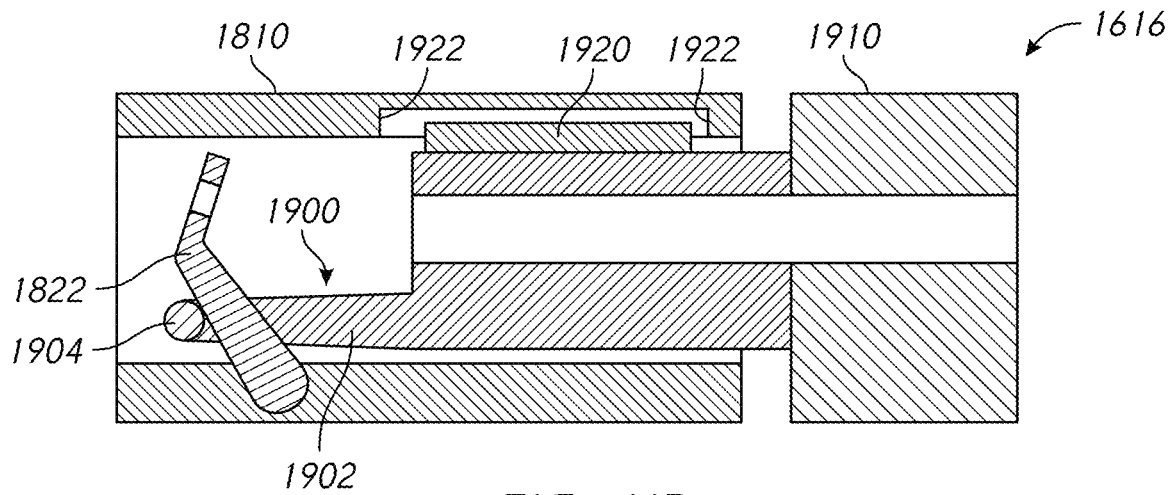
FIG. 11B illustrates the directional lock of FIG. 11A in an intermediate position.
Figure 11C:
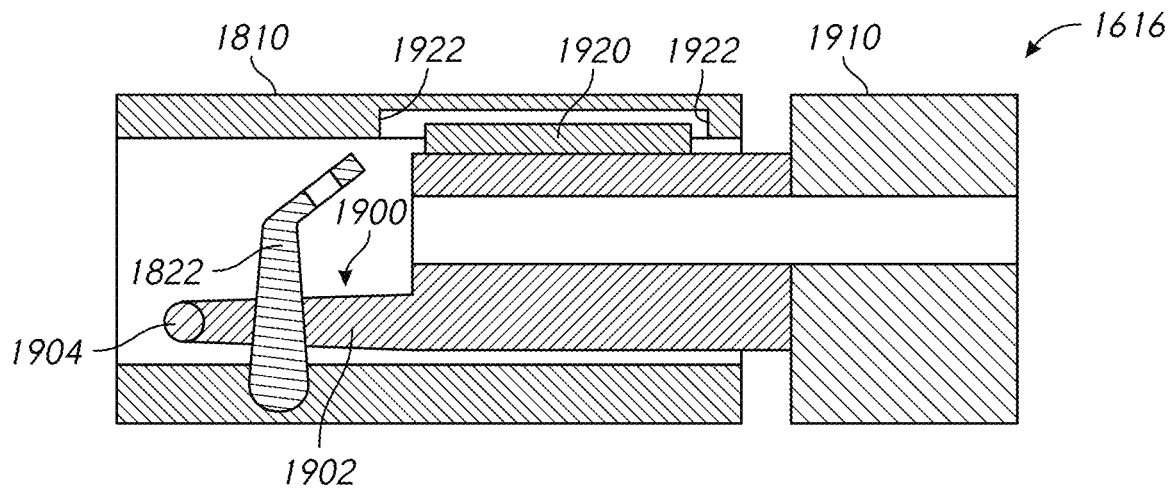
FIG. 11C illustrates the directional lock of FIG. 11A in a locked position.
Figure 12A:
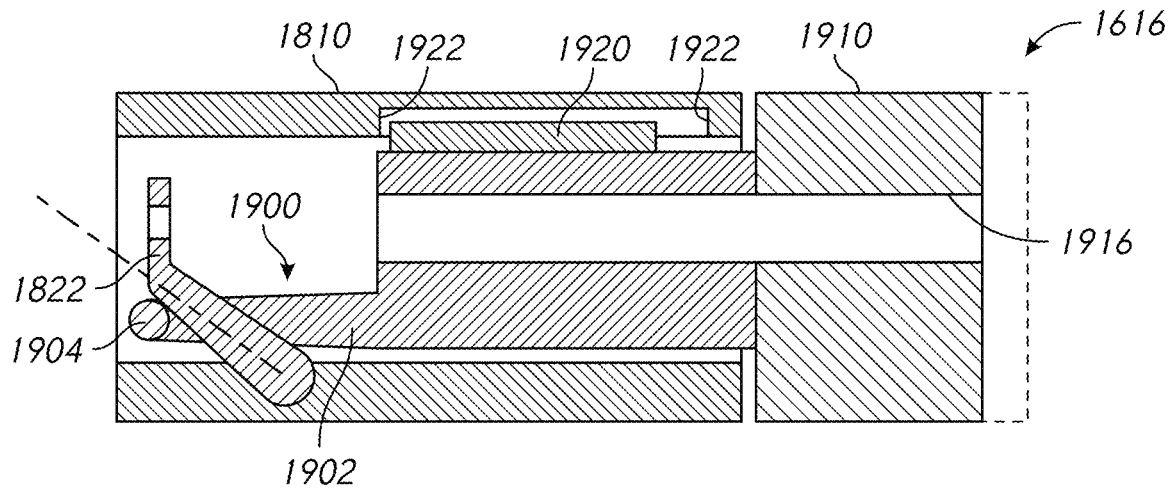
FIG. 12A is a longitudinal sectional view of the directional lock of FIG. 6A in a released position.
Figure 12B:
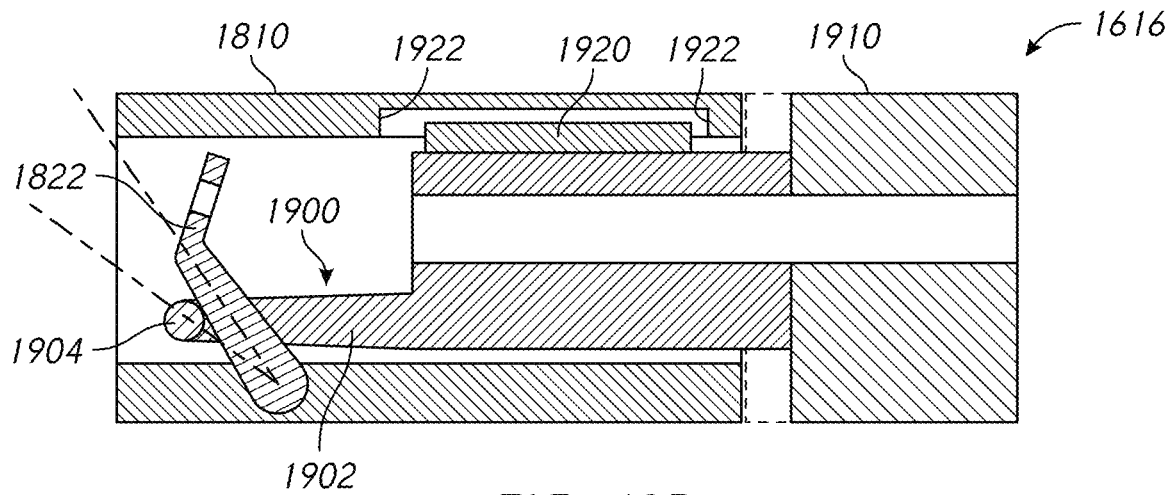
FIG. 12B illustrates the directional lock of FIG. 12A in an intermediate position.
Figure 12C:
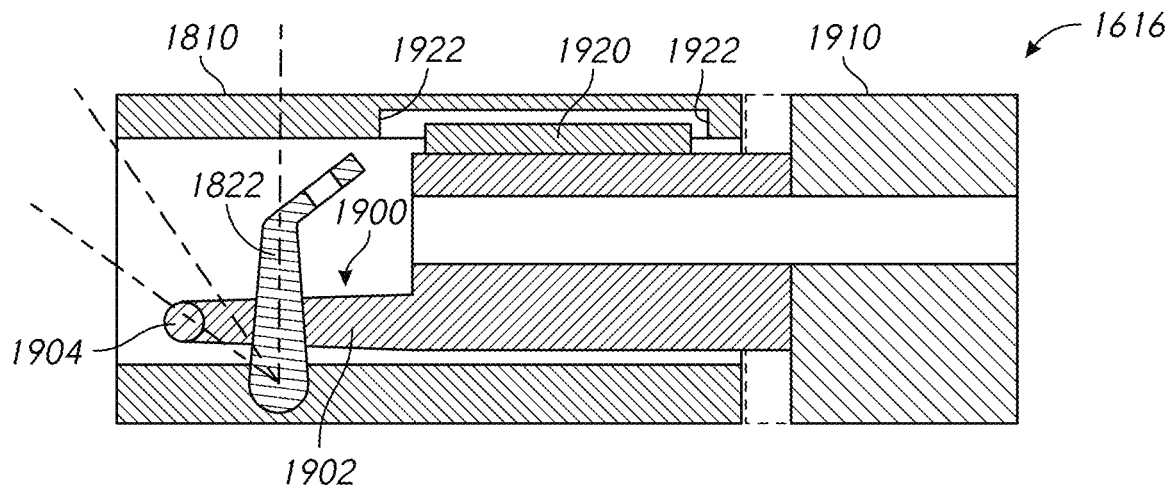
FIG. 12C illustrates the directional lock of FIG. 12A in a locked position.

With reference to FIGS. 11A-C and 12A-C, the catch 1900 does not necessarily move the lock washer 1822 all the way to the locked position. That is, in at least some configurations, the catch 1900 is capable of less movement than the lock washer 1822 such that the lock washer 1822 moves away from the catch end 1904 to the locked position. FIGS. 11A and 12A correspond to the position of FIG. 6A. FIGS. 11B and 12B correspond to the position of FIG. 6B. FIGS. 11C and 12C illustrate the lock washer 1822 having moved away from the catch end 1904 and to the locked position. FIGS. 12A, 12B and 12C include dashed lines illustrating the different positions of the lock washer 1822. FIGS. 12A, 12B and 12C also include dashed lines illustrating movement of the sleeve 1910 relative to the housing 1810.

In FIGS. 11A-C and 12A-C, a space is illustrated between the stops 1922 of the displacement slot 1924 and the stop guide 1920 for clarity. However, preferably, the end of the stop guide 1920 contacts each of the stops 1922 to limit movement of the sleeve 1910.

Figure 13:
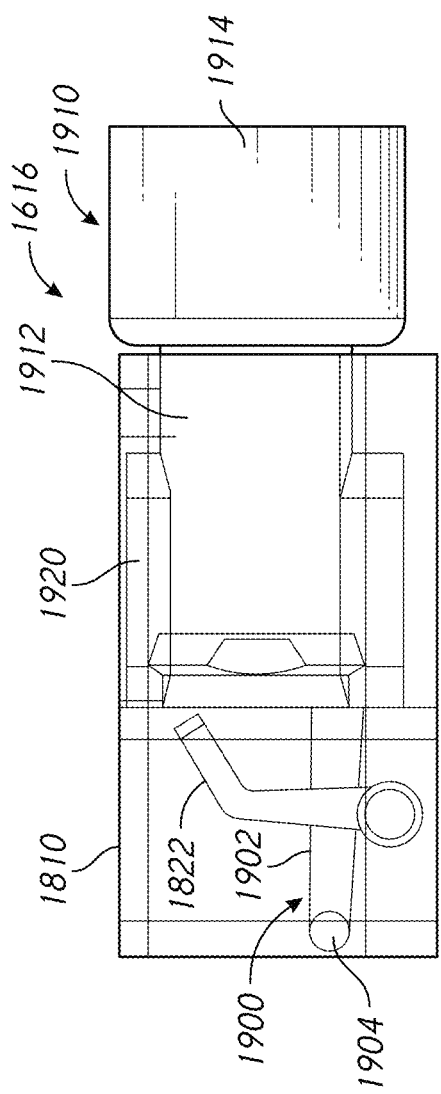
FIG. 13 is a side view of the directional lock of FIGS. 12A-12C. The outer housing of the directional lock is shown as transparent to show the underlying sleeve and lock member.

FIG. 13 illustrates the lock washer 1822 in a locked position and the sleeve 1910 in a released position relative to the housing 1810. In at least some configurations, the catch arrangement 1900 assists only in activation of the lock washer 1822 (movement of the lock washer 1822 from the released position toward the locked position), but does not assist in movement of the lock washer in a direction from the locked position toward the released position. However, in other arrangements, the catch arrangement 1900 could be configured to assist in release of the lock washer or both activation and release.

Although the pivot axis of the lock washer 1822 described in connection with FIGS. 5A-5D is fixed (within the bush 1852), arrangements are possible in which the pivot axis of the lock washer 1822 is not fixed. For example, the pivot axis of the lock washer 1822 may be configured to float relative to the housing 1810. As illustrated in FIGS. 6A and 6B, a position of the shaft 1824 of the lock washer 1822 can move relative to the housing 1810 between the released position of FIG. 6A and the partially locked position of FIG. 6B. For example, the shaft 1824 can slide relative to the housing 1810. In some configurations, the shaft 1824 can be captured in a slot, which allows the shaft 1824 to slide along the housing 1810, but restrains the shaft 1824 in other directions.

Rack and Pinion Mechanism

FIGS. 14-20 illustrate a modification of the directional lock 1616 of FIGS. 2-5D, which may be incorporated in a headgear or headgear and interface, such as the headgear 1600 and any of the interfaces 1650, 1660, 1670 of FIGS. 2-4. Thus, portions of the directional lock 1616, headgear or interface not specifically described in connection with FIGS. 14-20 may be similar to corresponding structure of FIGS.

2-5D, or may be of another suitable arrangement. The same reference numbers are used to refer to the same or corresponding components or features between the directional lock 1616 of FIGS. 2-5D and the directional lock 1616 of FIGS. 14-20.

Housing

The rack and pinion mechanism 2010 of FIGS. 14-20 includes a housing 2012, a pinion 2014, a shaft 2016, a rack 2018 and a brake 2020. As shown in FIGS. 15 and 16A-D, the housing 2012 is a substantially rectangular cuboid having rounded edges and is configured to house the pinion 2014, shaft 2016, brake 2020 and at least part of the rack 2018 and comprises a pinion aperture 2022 on the top surface that opens into an internal chamber 2024 that is configured to receive the pinion 2014. The internal chamber 2024 makes the housing 2012 substantially hollow having front, back, left side and bottom walls 2026F, 2026BA, 2026L, 2026BO that are approximately the same thickness and a right side wall 2026R that is thicker than the other walls.

A shaft aperture 2028 extends through each of the front and back walls 2026F, 2026BA of the housing 2012, and is configured to receive and retain the shaft 2016. The shaft aperture 2028 is stadium shaped with a height H that is approximately the same as the diameter of the shaft 2016 and has a length L that is longer than the diameter of the shaft 2016, such that the shaft 2016 may slide along the length of the shaft aperture 2028.

A rack aperture 2030 (i.e., first and second openings) extends through each of the left and right side walls 2026L, 2026R of the housing 2012. The rack apertures 2030 are square or rectangular and are large enough for the rack 2018 to pass through them. The rack aperture 2030 of the left wall 2026L is aligned with the rack aperture 2030 of the right wall 2026R such that the path of the rack 2018 is straight. The rack aperture 2030 is positioned such that the rack 2018 passes beneath the pinion 2014.

A brake aperture 2032 extends between the front and back walls 2026F, 2026BA and cuts into the right side wall 2026R. The brake aperture 2032 has a profile that matches the cross-section of the brake 2020 and is configured to receive and retain the brake 2020. The right side wall 2026E is thicker than the other walls to accommodate the thickness of the brake aperture 2032 and brake 2020.

Rack and Pinion

As shown in FIG. 17, the pinion 2014 comprises a centrally located gear 2034 which is flanked on each side by a circular flange 2036 that has a larger diameter than the outer diameter of the gear teeth 2038. The cylindrical shaft 2016 extends axially through the pinion 2014, protruding from the outer walls of the pinion 2014 and provides a rotational linkage between the pinion 2014 and the housing 2012. The shaft 2016 and pinion 2014 are press fitted together such that there is no relative movement (rotation) between them. In alternative embodiments, the shaft 2016 and pinion 2014 may be formed as a single integral component. In some embodiments the circular flanges 2036 may be formed independently of the gear 2034 and shaft 2016 and assembled together as a secondary step.

The rack 2018 can be functionally similar to the above-described core member and may be referred to as a core member herein. The rack 2018 is elongate and comprises a plurality of teeth 2040 along one side that are configured to mesh with the teeth 2038 of the gear 2034, such that linear movement of the rack 2018 is translated into rotational movement of the pinion 2014. The rack 2018 has a free end 2042 and a fixed end 2044. When assembled with the housing 2012, the fixed end 2044 is proximal to the brake 2020 and the free end 2042 is proximal to the pinion 2014. The fixed end 2044 is configured to be integrally formed with or permanently joined to another mask component such as a frame or headgear arrangement. The free end 2042 is configured to remain unattached such that it may move relative to other mask components.

In some embodiments the fixed end 2044 of the rack 2018 is integrally formed or permanently joined with a headgear strap. This arrangement provides a strap element for the headgear that can be lengthened or shortened, relative to a frame or other mask component that includes the housing, thus allowing the headgear size to be adjusted. Alternatively, the fixed end of the rack may be integral with or permanently joined to a mask frame or other mask component and the housing may be fixed to a headgear strap.

Brake

Figure 16:
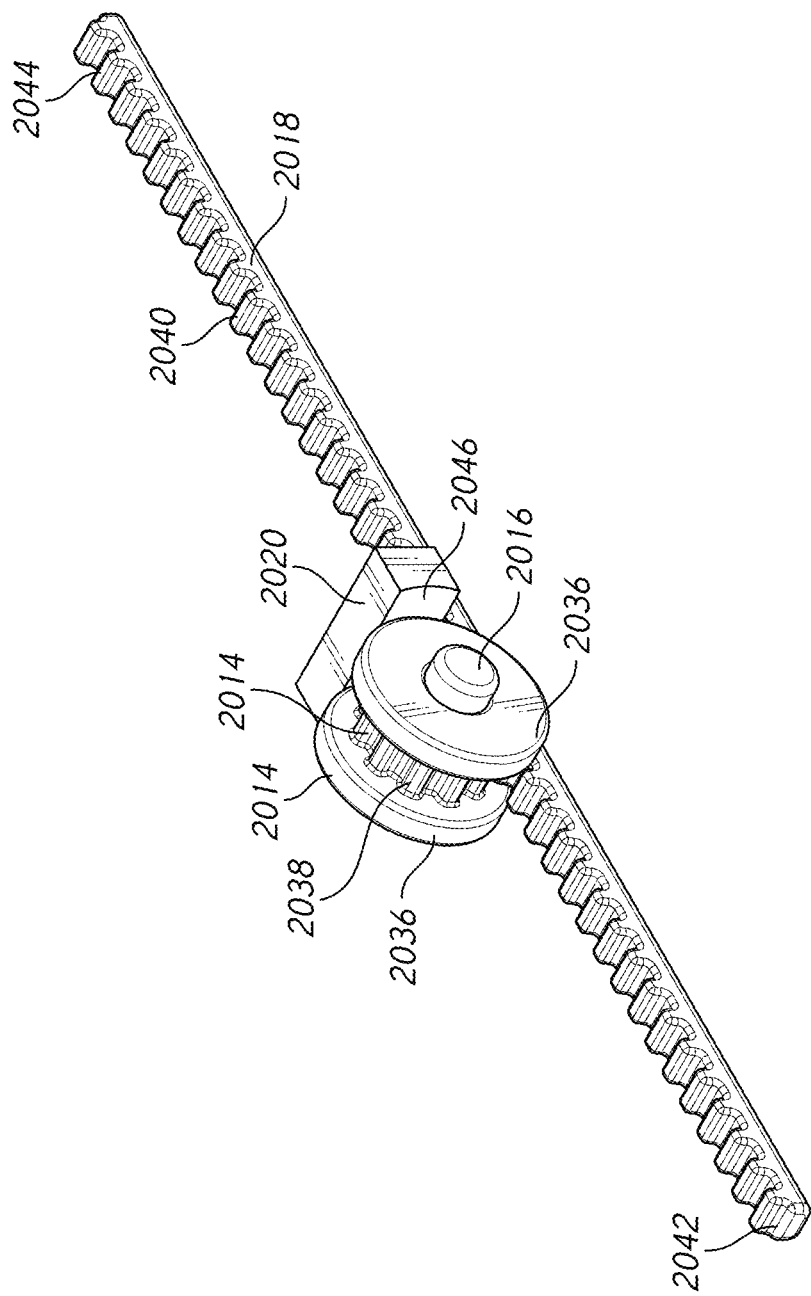
FIG. 16 is an isometric view of the rack and pinion mechanism without the housing to illustrate the brake and the rack and pinion mechanisms.
Figure 21:
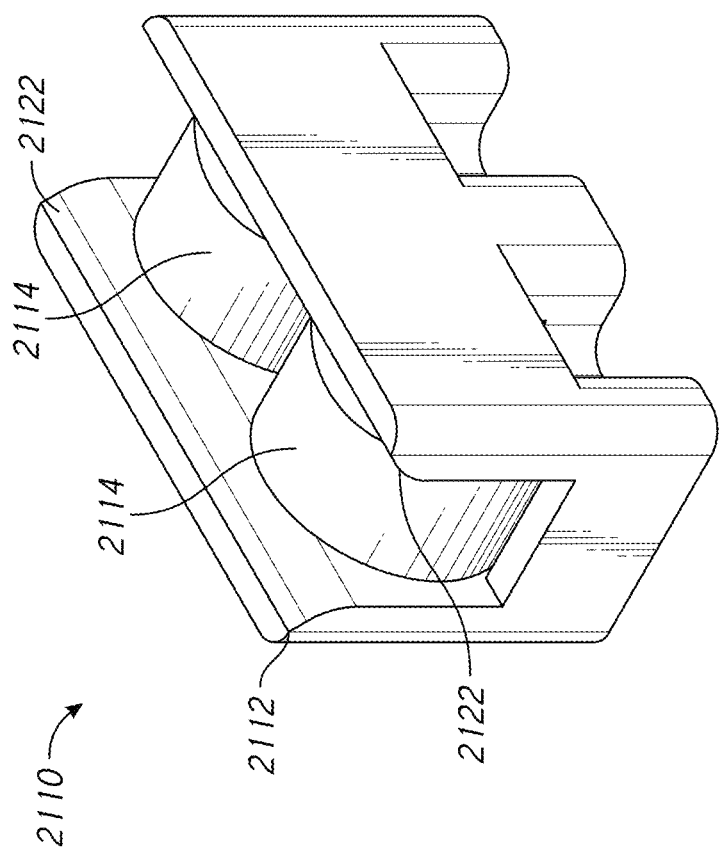
FIG. 21 is an isometric view of an exemplary roller lock mechanism.

As illustrated in FIG. 16, the brake 2020 comprises an extrusion that is substantially rectangular in cross-section but includes one side wall 2046 that is concave. The concave side 2046 has a diameter that substantially matches the outer diameter of the flanges 2036 of the pinion 2014. The concave side 2046 of the brake 2020 protrudes from the internal surface of the right wall 2026R of the housing 2012. The brake 2020 can be made of a soft and compressible material such as an elastomeric plastic or rubber.

Retraction

FIGS. 17 and 18 show the positioning of the pinion 2014 relative to the housing 2012 during a retraction movement of the rack 2018. In a retraction movement of the rack 2018, the fixed end 2044 of the rack 2018 is moved towards the housing 2012 and thus the free end 2042 moves away from the housing 2012. This movement would result in the reduction of the length of the headgear when combined in such an arrangement as described earlier.

During this retraction movement the linear movement of the rack 2018 causes the teeth 2040 of the rack 2018 to mesh with the teeth 2038 of the gear 2034 and rotate the pinion 2014 in a clockwise direction (relative to the page). This rotation also pushes the pinion 2014 towards the left side wall 2026L of the housing 2012, and keeps the shaft 2016 at the left end of the shaft aperture 2028. The internal surface of the left side wall 2026L is curved in a region immediately above the rack aperture 2030 to substantially match the outer diameter of the pinion 2014. This reduces friction between the pinion 2014 and the housing 2012 and allows the rack 2018 to move freely through the housing 2012. In this position, there is clearance between the pinion 2014 and the concave wall 2046 of the brake 2020.

In some embodiments the rack and pinion mechanism 2010 can be combined with a biasing means such as an elastic strap that provides a retraction force that biases the rack to move in the retraction direction without the user applying an external force.

There is a gap between the flanges 2036 and the left side wall 2026L of the housing 2012. This allows a low level of friction between the pinion 2014 and the rack 2018 during retraction. In alternative embodiments, the internal geometry of the left side wall 2026L can be different as it does not affect the functionality of the mechanism. In some cases, the left side wall 2026L need not exist.

Extension

FIGS. 19 and 20 show the positioning of the pinion 2014 relative to the housing 2012 (and other components) during an extension movement of the rack 2018. In an extension movement of the rack 2018, the fixed end 2044 of the rack 2018 is moved away from the housing 2012 and thus the free end 2042 moves towards the housing 2012. This movement would result in an extension in the length of the headgear when combined in such an arrangement as described earlier.

During this extension movement the linear movement of the rack 2018 causes the teeth 2038 of the rack 2018 to mesh with the teeth 2038 of the gear 2034 and rotate the pinion 2014 in an anticlockwise direction (relative to the page). This rotation also pushes the pinion 2014 towards the right side wall 2026R of the housing 2012 and the brake 2020. The shaft 2016 slides towards the right side of the shaft aperture 2028 such that the flanges 2036 of the pinion 2014 contact the concave wall 2046 of the brake 2020 and compress the brake 2020. This provides friction between the pinion 2014 and the brake 2020 which prevents the rack 2018 from moving freely through the housing 2012. The concave wall 2046 of the brake 2020 allows the pinion 2014 to continue to rotate in response to the linear movement of the rack 2018, but a higher force is required to induce this.

When combined within a mask arrangement this results in a resistance to elongation of the headgear, which requires the user to intentionally apply a large enough force to overcome the friction between the pinion and brake, in order to increase the size of the headgear.

Roller Lock Mechanism

FIGS. 21-25C illustrate a modification of the directional lock 1616 of FIGS. 2-5D, which can be incorporated in a headgear or headgear and interface, such as the headgear 1600 and any of the interfaces 1650, 1660, 1670 of FIGS. 2-4. Thus, portions of the directional lock 1616, headgear or interface not specifically described in connection with FIGS. 21-32 can be the same as or similar to corresponding structure of FIGS. 2-5D, or can be of another suitable arrangement. The same reference numbers are used to refer to the same or corresponding components or features between the directional lock 1616 of FIGS. 2-5D and the directional lock 1616 of FIGS. 21-25C.

Housing

The roller lock mechanism 2110 of FIGS. 21-25C includes a housing 2112, a pair of rollers 2114 and a filament (not shown). As shown in FIGS. 21-23D, the housing 2112 is a substantially rectangular cuboid having rounded edges in a vertical direction (relative to the page) and is configured to house and retain the pair of rollers 2114 such that a filament 2118 can pass between them and through the housing 2112. The housing 2112 comprises a central channel 2124 that extends laterally from one end of the housing to the other. The central channel 2124 defines a front wall 2126F, back wall 2126BA and a base portion 2150, such that the housing 2112 has a generally U-shaped cross-section when viewed from the side. The central channel 2124 is configured to receive the pair of rollers 2114.

The housing 2112 has axle slots or tracks 2128 that receive and retain the axles 2116 of the rollers 2114 such that the rollers 2114 can rotate about the axle 2116. The axle tracks 2128 comprise elongate rectangular slots that are cut into the inside of the front and back walls 2126F, 2126BA of the housing 2112. The axle tracks 2128 have a height H that is greater than the radius of the roller (Rr) plus the radius of the axle (Ra). That is, H>Rr+Ra. The axle tracks 2128 have a width W that is slightly wider than the diameter of the axle 2116.

The housing 2112 has a filament aperture 2130 that extends through the base portion 2150 of the housing 2112. The filament aperture 2130 is positioned such that it is half way between the two rollers 2114 and is configured to have the filament 2118 pass through it.

The housing 2112 has bearing surfaces 2120 that form a part of the base portion 2150 of housing 2112. The bearing surfaces 2120 are positioned towards the lateral sides of the base portion 2150 and form a lower internal surface of the central channel 2124. The bearing surfaces 2120 are angled towards each other such that a cradle geometry is formed on the upper surfaces of the base portion 2150. The cradle has a shape and geometry that is configured to receive a lower portion of the rollers 2114.

Other geometry features (such as the notches and apertures in the base portion 2150) are provided for manufacturability.

Rollers

Figure 24B:
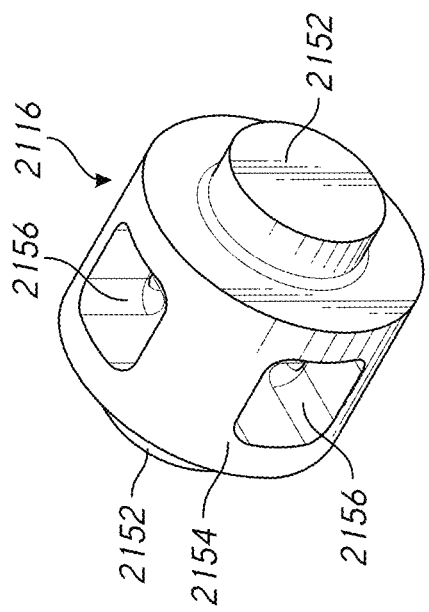
FIG. 24B is an isometric view of the axle of the exemplary roller lock mechanism.
Figure 24C:
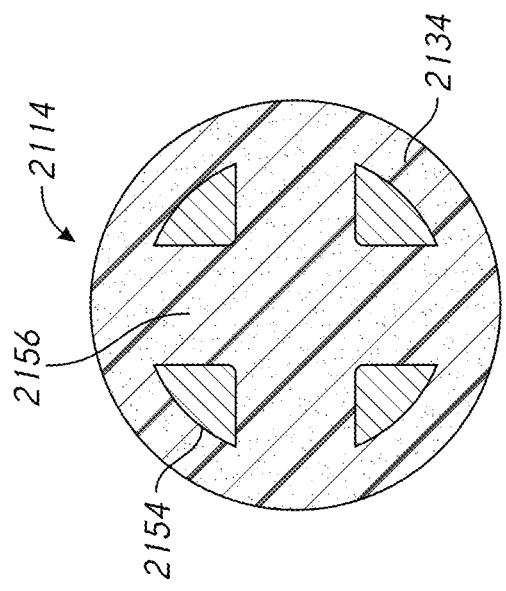
FIG. 24C is a cross-sectional side view of the roller of the exemplary roller lock mechanism.
Figure 24A:
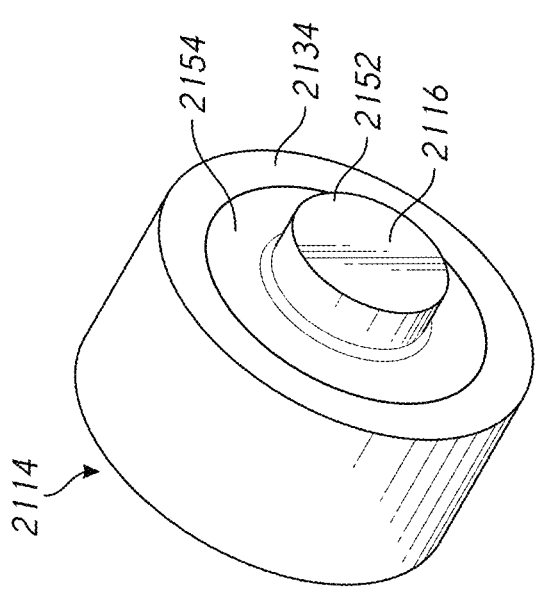
FIG. 24A is an isometric view of the roller of the exemplary roller lock mechanism.

As shown in FIGS. 24A to 24C, the rollers 2114 have a cylindrical shape and comprise an axle 2116 that is cylindrical, and forms the core of the rollers 2114. The axle 2116 comprises a pair of axle nubs 2152 that are spaced apart laterally by a central portion 2154. The axle nubs 2152 and central portion 2154 are axially aligned. The central portion 2154 comprises a cylindrical body having a greater diameter than the diameter of the axle nubs 2152. The central portion 2154 comprises a pair of hollow passages 2156 that extend through the diameter of the central portion 2154 of the axle 2116. The hollow passages 2156 are perpendicular to each other and intersect at the centre of the axle 2116 to form an internal cavity within the central portion 2154. The axle nubs 2152 are received by the axle retention recesses in the housing 2112.

The rollers 2114 have a tread 2134 that comprises an elastomeric, compressible and tactile material. Such materials increase friction between the rollers 2114 and the filament 2118 and/or housing. The tread 2134 surrounds the central portion 2154 of the axle 2116. The tread 2134 can be over-moulded onto the axle 2116 such that a mechanical and/or chemical connection is formed between the two. The material of the tread 2134 is configured to fill the hollow passages 2156 of the axle 2116 to provide a mechanical connection between the tread 2134 and the axle 2116. In some configurations, an outer surface of the roller 2114 may be formed from an elastomeric, compressible and tactile material to increase friction between the rollers 2114 and the filament 2118 and/or housing 2112.

Filament

The filament 2118 can be functionally similar to the above-described core member and can be referred to as a core member herein. The filament 2118 is elongate and may be integrally formed or permanently connected to a headgear structure or other mask component at a fixed end 2144. The filament 2118 has an opposing free end 2142 that provides a means for extending the length of a headgear strap or otherwise increasing the size of mask assembly. The filament 2118 can be a material such as nylon fishing line. The filament 2118 is configured to pass between and interact with the rollers 2114 and passes through the central channel 2124 and filament aperture 2130 in the housing 2112.

Roller Lock Operation

FIG. 25A shows the roller lock mechanism 2110 in a retraction mode wherein the size of the headgear or mask is reduced, in use. In the retraction mode the filament 2118 is free to move towards the left. Rollers 2114 rotate or roll in unison with the filament 2118, in the direction indicated by the arrows. The free movement of the filament 2118 allows the size of the headgear/mask to be reduced with little effort. The elastomeric tread 2134 of the rollers 2114 is configured to provide a level of friction between the tread 2134 and filament 2118 that causes the axle nubs 2152 to slide within the axle tracks 2128 towards the left (or away from the base portion 2150). In this position friction between the rollers 2114 and the housing 2112 is minimal and thus the force required to move the filament 2118 through the mechanism is also minimal. A biasing means may be attached to the filament 2118 such that it applies a retraction force great enough to pull the filament 2118 through the mechanism to reduce the headgear size. For example, the biasing means may comprise an elastic strap connected between the headgear and mask frame.

FIGS. 25B and 25C show the mechanism in an extension mode, wherein the size of the headgear or mask is increased. In the extension mode the filament 2118 is restricted in moving to the right. The friction between the tread 2134 and the filament 2118 causes the axles 2116 to slide within the axle tracks 2128 towards the right (or towards the base portion 2150) until the tread 2134 hits the base portion 2150 of the housing 2112. When the tread 2134 contacts the base portion 2150 the rollers 2114 stop rotating/rolling due to friction and the filament 2118 slips between the rollers 2114. The force required to pull the filament 2118 between the rollers 2114 in an extension mode is greater than in a retraction mode. This is because the friction between the filament 2118 and rollers 2114 is increased when the rotation of the rollers 2114 is resisted.

FIG. 25C illustrates the bearing surfaces 2120. The bearing surfaces 2120 further enhance the friction between the filament 2118 and the rollers 2114 by increasing the friction between the tread 2134 and the base portion 2150. An increased contact area between the tread 2134 of the rollers 2114 and the base portion 2150 is provided by the bearing surfaces 2120; which in turn increases the friction between them and the resistance to rotation. The bearing surfaces 2120 not only restrict the rotational freedom of the rollers 2114 but force them closer together and towards the filament 2118, which creates more friction and interference between tread 2134 and the filament 2118.

In the roller lock mechanism, there is deliberate interference between the tread 2134 and the filament 2118, even in the free rolling/retraction mode. This is to ensure the roller 2114 will traverse/slide in its track 2128 when the core changes direction. This movement activates or releases the lock. There is also deliberate play between the axle nubs 2152 and the axle tracks 2128, which allows the rollers 2114 to be forced together, by the bearing surfaces 2120, and increase the interference with the filament 2118.

In other configurations, the roller lock mechanism may include a single roller. In such an arrangement, the filament is supported on one side by the housing and is engaged with the roller on the other side. In a retraction mode, a bearing surface may force the roller towards the filament such that the filament is wedged between the roller and the housing. Accordingly, movement of the filament is inhibited.

Variations of Rack and Pinion Mechanisms

FIGS. 26A-28D illustrate variations of the rack and pinion mechanism of FIGS. 14-20, which may be incorporated in a headgear or headgear and interface, such as the headgear 1600 and any of the interfaces 1650, 1660, 1670 of FIGS. 2-4. Thus, portions of the rack and pinion mechanism 2010, headgear or interface not specifically described in connection with FIGS. 33-36 may be similar to corresponding structure of FIGS. 14-20, or may be of another suitable arrangement. The same reference numbers are used to refer to the same or corresponding components or features between the rack and pinion mechanism 2010 of FIGS. 14-20 and the rack and pinion mechanisms 2210, 2310, 2410 of FIGS. 33-36.

Figure 14:
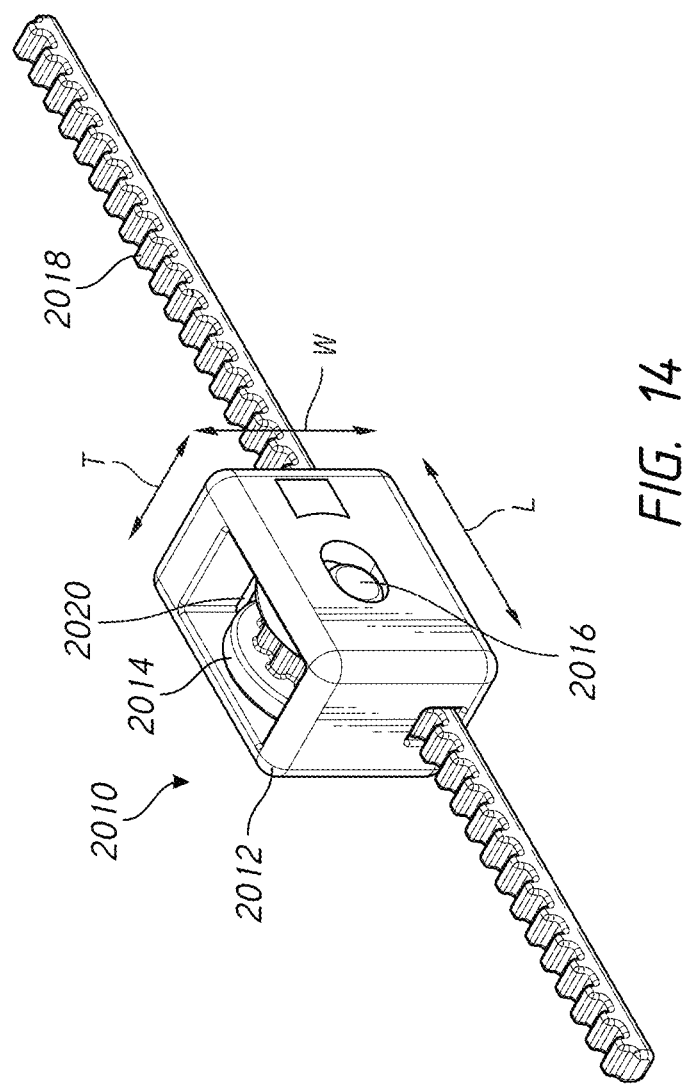
FIG. 14 is an isometric view of an exemplary rack and pinion mechanism.
Figure 15B:
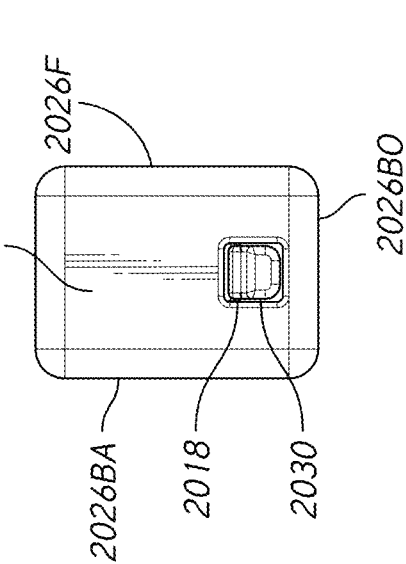
FIG. 15B is a right-side view of the exemplary rack and pinion mechanism in FIG. 14.
Figure 15A:
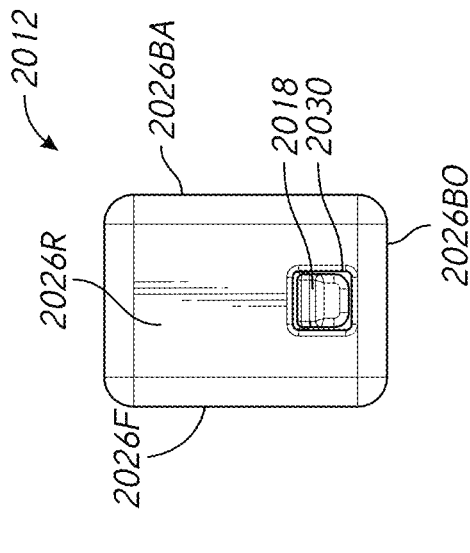
FIG. 15A is a front view of the exemplary rack and pinion mechanism in FIG. 14.
Figure 15C:
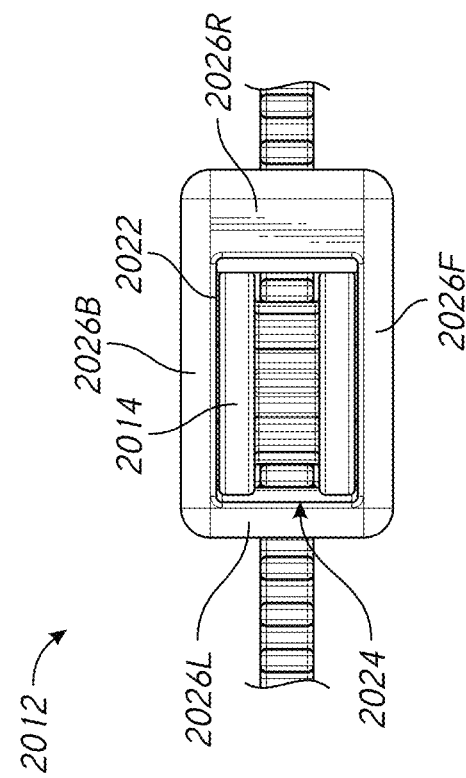
FIG. 15C is a left-side view of the exemplary rack and pinion mechanism in FIG. 14.
Figure 15D:
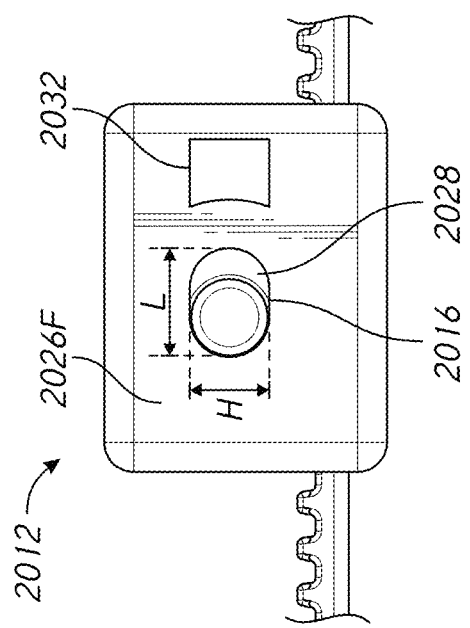
FIG. 15D is a top-side view of the exemplary rack and pinion mechanism in FIG. 14.

The rack and pinion mechanism 2010 in FIG. 14 includes dimension lines indicating the measurements for thickness T, length L and width W of the rack and pinion mechanism 2010. In a preferred embodiment, the housing 2012 may have a thickness T of 7.2 mm, a length L of 12.5 mm and a width W of 9.6 mm and the rack 2018 may have a thickness T of 1.8 mm and a width W of 9.6 mm.

FIGS. 25A to 25D illustrate an alternative rack and pinion mechanism 2210 having a housing 2010 and a rack 2018 that are comparatively compact and reduced in size. In a preferred embodiment, the rack 2018 may have a thickness T of 0.8 mm and a width W of 1.375 mm. The compact dimensions of the rack 2018 allow the rack 2018 to flex in at least the direction of its thickness and width. The compact dimensions of the rack 2018 also allow for a reduction in the dimensions of the housing 2012. In the preferred embodiment, the housing 2012 may have a thickness T of 4.8 mm, a length L of 11.0 mm and a width W of 9.0 mm. The reduction in the size of the housing 2012 and the rack 2018 may provide a smaller form factor such that the headgear and masks fitted with the compact rack and pinion mechanism 2210 may be less bulky and cumbersome.

FIGS. 26A to 26D illustrate another alternative rack and pinion mechanism 2310 having a comparatively thicker rack 2018. In a preferred embodiment, the rack 2018 may have a thickness T of 5.8 mm and a width W of 1.375 mm. The increased thickness of the rack 2018 provides, at least, an increase in the rigidity of the rack 2018 in the direction of its thickness such that bending in the direction of its thickness is resisted. The width W of rack 2018 allows bending in the direction of its width. The thickness of the housing 2012 is also correspondingly increased to accommodate the additional thickness of the rack 2018. In the preferred embodiment, the housing 2012 may have a thickness T of 9.8 mm, a length L of 11.0 mm and a width W of 9.0 mm.

In some embodiments, the rack and pinion mechanism 2310 can be arranged and/or oriented in a headgear such that the teeth of the rack face away from a user's face, in use. Accordingly, the rack 2018 is oriented such that the increased thickness of the rack 2018 inhibits or prevents upward and downward flexing of the rack 2018 relative to the user's head while allowing flexing of the rack 2018 towards or away from a user's face. This allows the headgear to be adaptable to different head shapes and sizes while providing increased support to a mask.

FIGS. 27A to 27D illustrate yet another alternative rack and pinion mechanism 2410 having a rack 2018 that is comparatively wider. In a preferred embodiment, the rack 2018 may have a thickness T of 0.8 mm and a width W of 6.375 mm. The increased width of the rack 2018 provides, at least, an increase in rigidity of the rack 2018 in the direction of its width such that bending in the direction of its width is resisted. The thickness T of the rack 2018 allows bending in the direction of its thickness. In the preferred embodiment, the housing 2012 may have a thickness T of 4.8 mm, a length L of 11.0 mm and a width W of 14.0 mm.

In some embodiments, the rack and pinion mechanism 2410 can be arranged and/or oriented in a headgear such that the teeth of the rack are normal to a user's face, in use. Accordingly, the rack 2018 is oriented such that the increased thickness of the rack 2018 inhibits or prevents upward and downward flexing of the rack 2018 relative to the user's head while allowing flexing of the rack 2018 towards or away from a user's face. This allows the headgear to be adaptable to different head shapes and sizes while providing increased support to a mask. This orientation may also reduce the distance that the rack and pinion mechanism 2410 and the headgear protrude outward and away from the head of the user, which may reduce bulkiness and provide the headgear with a lower profile.

In each of the rack and pinion mechanisms 2210, 2310, 2410, the housing 2012 has an open end 2026N that allows the length of the housing 2012 to be reduced. That is, in contrast to the rack and pinion mechanism 2010, the rack and pinion mechanisms 2210, 2310, 2410 do not include a left side wall 2026L. As shown, the housing 2012 is configured such that a circumferential edge of the pinion 2014 is substantially aligned with and tangent to the edge of the housing 2012. The open end 2026N reduces the length L and bulk of the housing 2012 and the amount of material used to manufacture the housing 2012, which provides a smaller, lighter and lower cost component.

In some configurations, the rack and pinion mechanisms 2210, 2310, 2410 may be oriented in different directions relative to the headgear that it is attached to or incorporated with. In some configurations, the thicknesses and widths of the housing and the rack may vary from the preferred embodiments according to the desired size and profile of the rack and housing, the load capacity and bending characteristics of the rack, etc.

In some configurations, the rack and pinion mechanism is arranged on the headgear such that the teeth of the rack are normal to the user's face when the width of the rack is greater than the thickness of the rack. In other configurations, the rack and pinion mechanism is arranged on the headgear such that the teeth of the rack face away from the user's face when the thickness of the rack is greater than the width of the rack. In some configurations, the rack and pinion mechanism is arranged on the headgear such that the width (length in cross-section) of the side of a user-facing portion of the rack is greater than the width of the side of a portion of the rack that is normal to the user's face. That is, the portion of the rack contacting the user's face is wider than the portion of the rack that is normal to the user's face.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A directional lock, comprising:
   a housing defining an interior space, a first opening and a second opening, wherein each of the first and second openings communicates with the interior space;
   a brake defined by or supported by the housing;
   at least one lock disposed within the housing;
   a core that passes through both the first and second openings of the housing and engages the at least one lock such that movement of the core relative to the housing causes rotation of the at least one lock;
   wherein the at least one lock is movable relative to the housing between a first position, which provides a first level of resistance to rotation of the at least one lock, and a second position, which provides a second level of resistance to rotation of the at least one lock, wherein the second level of resistance is higher than the first level; and
   wherein the second level of resistance is caused at least in part by contact between the at least one lock and the brake.

2. The directional lock of claim 1, wherein the first and second openings of the housing are aligned.

3. The directional lock of claim 1, wherein the housing comprises a left side wall and a right side wall, wherein the right side wall is thicker than the left side wall, and wherein the first opening and the second opening extend through the left and right side walls respectively.

4. The directional lock of claim 2, wherein the housing further comprises a Front wall, a back wall, a top wall, and a bottom wall, and wherein the top wall comprises a third opening that opens into the interior space of the housing.

5. The directional lock of claim 1, wherein the at least one lock comprises a pinion and a shaft.

6. The directional lock of claim 5, wherein the housing further comprises:
   a shaft aperture extending through openings in each of the front and back walls configured to receive and retain the shaft; and
   a brake aperture extending through openings in each of the front and back walls and which is configured to receive and retain the brake.

7. The directional lock of claim 5, wherein the pinion comprises a centrally located gear including gear teeth, the centrally located gear being flanked on each side by a circular flange that has a larger diameter than an outer diameter of the gear teeth.

8. The directional lock of claim 5, wherein the shaft is cylindrical and extends axially through the pinion and provides a rotational linkage between the pinion and the housing.

9. The directional lock of claim 7, wherein the circular flanges are formed independently of the centrally located gear and shaft.

10. The directional lock of claim 7, wherein the core is elongate and comprises a plurality of teeth along one side that are configured to mesh with the gear teeth of the gear.

11. The directional lock of claim 5, wherein the core has a first end proximal to the brake and a second end proximal to the pinion, and wherein the first end is configured to be integrally formed with or permanently joined to another component, and the second end is configured to remain unattached.

12. The directional lock of claim 11, wherein the first end of the core is integrally formed or permanently joined with a headgear strap, and wherein the housing is fixed to a mask frame or mask component.

13. The directional lock of claim 7, wherein the brake is substantially rectangular in cross-section but includes one side wall that is concave, the concave side wall having a diameter that substantially matches the outer diameter of the flanges of the pinion.

14. The directional lock of claim 6, wherein the shaft aperture is stadium shaped with a height that is approximately the same as the diameter of the shaft and a length that is longer than a diameter of the shaft, such that the shaft is configured to slide along the length of the shaft aperture.

15. The directional lock of claim 1, further comprising a biasing means that is configured to bias movement of the core relative to the housing.

16. The directional lock of claim 15, wherein the biasing means comprises an elastic strap.

17. The directional lock of claim 15, wherein the biasing means is configured to bias movement of the core such that a first end of the core is moved toward the brake.

18. The directional lock of claim 1, wherein the brake is made of a soft and compressible material.

19. The directional lock of claim 18, wherein the soft and compressible material comprises an elastomeric plastic or rubber.

* * * * *

UNITED STATES PATENT AND TRADEMARK OFFICE
CERTIFICATE OF CORRECTION

| | | |
|---|---|---|
| PATENT NO. | : 11,819,620 B2 | |
| APPLICATION NO. | : 18/171159 | |
| DATED | : November 21, 2023 | |
| INVENTOR(S) | : Jeroen Hammer et al. | |

It is certified that error appears in the above-identified patent and that said Letters Patent is hereby corrected as shown below:

On the Title Page

Page 6, Column 1 item (56) (Other Publications), Line 1, delete "Pas" and insert -- Pad --.

Page 6, Column 1 item (56) (Other Publications), Line 6, delete "cpapexhange" and insert -- cpapxchange --.

In the Specification

Column 8, Line 56, delete "NW," and insert -- NIV, --.

In the Claims

Column 29, Line 34, Claim 4, delete "Front" and insert -- front --.

Signed and Sealed this
Twenty-third Day of January, 2024

Katherine Kelly Vidal
*Director of the United States Patent and Trademark Office*